(12) United States Patent
Handique et al.

(10) Patent No.: US 11,547,995 B2
(45) Date of Patent: Jan. 10, 2023

(54) SYSTEM AND METHOD FOR RAPID MULTIPLEXED SAMPLE PROCESSING WITH APPLICATIONS FOR NUCLEIC ACID AMPLIFICATION ASSAYS

(71) Applicant: Bio-Rad Laboratories, Inc., Hercules, CA (US)

(72) Inventors: Kalyan Handique, Hercules, CA (US); Ronald Lebofsky, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 17/499,529

(22) Filed: Oct. 12, 2021

(65) Prior Publication Data
US 2022/0118442 A1   Apr. 21, 2022

Related U.S. Application Data

(60) Provisional application No. 63/093,727, filed on Oct. 19, 2020.

(51) Int. Cl.
*B01L 3/00* (2006.01)
*B01L 7/00* (2006.01)
*C12Q 1/686* (2018.01)

(52) U.S. Cl.
CPC ............ *B01L 3/50255* (2013.01); *B01L 7/52* (2013.01); *C12Q 1/686* (2013.01); *B01L 2200/021* (2013.01); *B01L 2200/026* (2013.01); *B01L 2200/0652* (2013.01); *B01L 2200/0689* (2013.01); *B01L 2300/041* (2013.01); *B01L 2300/046* (2013.01); *B01L 2300/069* (2013.01); *B01L 2300/0819* (2013.01); *B01L 2300/0893* (2013.01); *B01L 2300/168* (2013.01); *B01L 2300/18* (2013.01); *B01L 2300/1816* (2013.01)

(58) Field of Classification Search
CPC ......... B01L 2200/021; B01L 2300/041; B01L 2300/046
USPC ................................................. 422/552, 551
See application file for complete search history.

(56) References Cited

U.S. PATENT DOCUMENTS

| | | | |
|---|---|---|---|
| 5,965,452 A | 10/1999 | Kovacs | |
| 6,429,027 B1 | 8/2002 | Chee et al. | |
| 6,723,290 B1 | 4/2004 | Wardlaw | |
| 6,828,100 B1 | 12/2004 | Ronaghi | |
| 7,731,901 B2 | 6/2010 | Wardlaw | |
| 8,029,745 B2 | 10/2011 | Hunter et al. | |

(Continued)

*Primary Examiner* — Natalia Levkovich
(74) *Attorney, Agent, or Firm* — Jeffrey Schox

(57) ABSTRACT

The invention(s) cover systems and methods for target detection in a multiplexed and rapid manner. Embodiments of the system can include: a base substrate; and an array of sample processing regions defined at a broad surface of the base substrate, wherein each of the array of sample processing regions includes: a set of microwell subarrays arranged in a gradient by volumetric capacity between an upstream end and a downstream end of each respective sample processing region, and a boundary separating each respective sample processing region from adjacent sample processing regions. The system can support methods, with example implementation by an automated platform, for returning preliminary results from a subset of microwells of the samples processing regions, as well as results pertaining to specific and non-specific amplification, for multiple targets of a sample.

12 Claims, 9 Drawing Sheets

TOP VIEW

CROSS-SECTIONAL VIEW

(56) References Cited

U.S. PATENT DOCUMENTS

| | | |
|---|---|---|
| 8,420,017 B2 | 4/2013 | Jones et al. |
| 8,846,415 B2 | 9/2014 | Duffy et al. |
| 9,463,431 B2 | 10/2016 | Love et al. |
| 9,482,662 B2 | 11/2016 | Duffy et al. |
| 9,809,838 B2 | 11/2017 | Walt et al. |
| 9,850,123 B2 | 12/2017 | Gu et al. |
| 9,885,701 B2 | 2/2018 | Xie et al. |
| 10,865,434 B2 | 12/2020 | Hallock et al. |
| 10,941,396 B2 | 3/2021 | Fu et al. |
| 2001/0024805 A1* | 9/2001 | Williams et al. ..... B01L 3/5085 435/29 |
| 2008/0305515 A1 | 12/2008 | Burgart et al. |
| 2009/0298116 A1 | 12/2009 | Fang et al. |
| 2010/0216228 A1 | 8/2010 | Love et al. |
| 2010/0301398 A1 | 12/2010 | Rothberg et al. |
| 2011/0003286 A1 | 1/2011 | Hanafusa et al. |
| 2012/0129208 A1 | 5/2012 | Khine et al. |
| 2014/0287423 A1 | 9/2014 | Nurse |
| 2016/0016169 A1 | 1/2016 | Ben-Yakar et al. |
| 2016/0175836 A1 | 6/2016 | Taylor et al. |
| 2016/0256870 A1 | 9/2016 | Ismagilov et al. |
| 2018/0002764 A1 | 1/2018 | Fan et al. |
| 2018/0250672 A1 | 9/2018 | Jamshidi et al. |
| 2019/0111424 A1 | 4/2019 | Chou et al. |
| 2019/0143328 A1 | 5/2019 | Savran et al. |
| 2019/0218497 A1 | 7/2019 | Boedicker et al. |

* cited by examiner

SYSTEM AND METHOD FOR RAPID MULTIPLEXED SAMPLE PROCESSING WITH APPLICATIONS FOR NUCLEIC ACID AMPLIFICATION ASSAYS

CROSS-REFERENCE TO RELATED APPLICATIONS

This application claims the benefit of U.S. Provisional Application No. 63/093,727 filed on 19 Oct. 2020, which is incorporated in its entirety herein by this reference.

TECHNICAL FIELD

This invention relates generally to the sample processing field, and more specifically to new and useful systems and methods for rapid and multiplexed sample processing, with applications in characterizing in performing nucleic acid amplification assays.

BACKGROUND

Detecting and characterizing targets from biological samples is relevant to many fields. However, sample processing involving partitioned sample volumes is typically time consuming, workflow-intensive, manual, and subject to cost constraints, motivating development of new technologies to address these and other deficiencies.

In particular, in the context of polymerase chain reaction (PCR) processes involving partitioned volumes (e.g., for digital PCR, for qPCR, etc.), partitioning of samples in an efficient manner that is not cost prohibitive, while increasing dynamic range of detection and multiplexing capability, is of interest. Current partitioning devices and systems, however, are typically expensive, require large device footprints, are limited in dynamic range, are limited in ability to perform multiplexed analysis, and require long processing times to produce results.

DESCRIPTION OF THE PREFERRED EMBODIMENTS

Figure 1A:
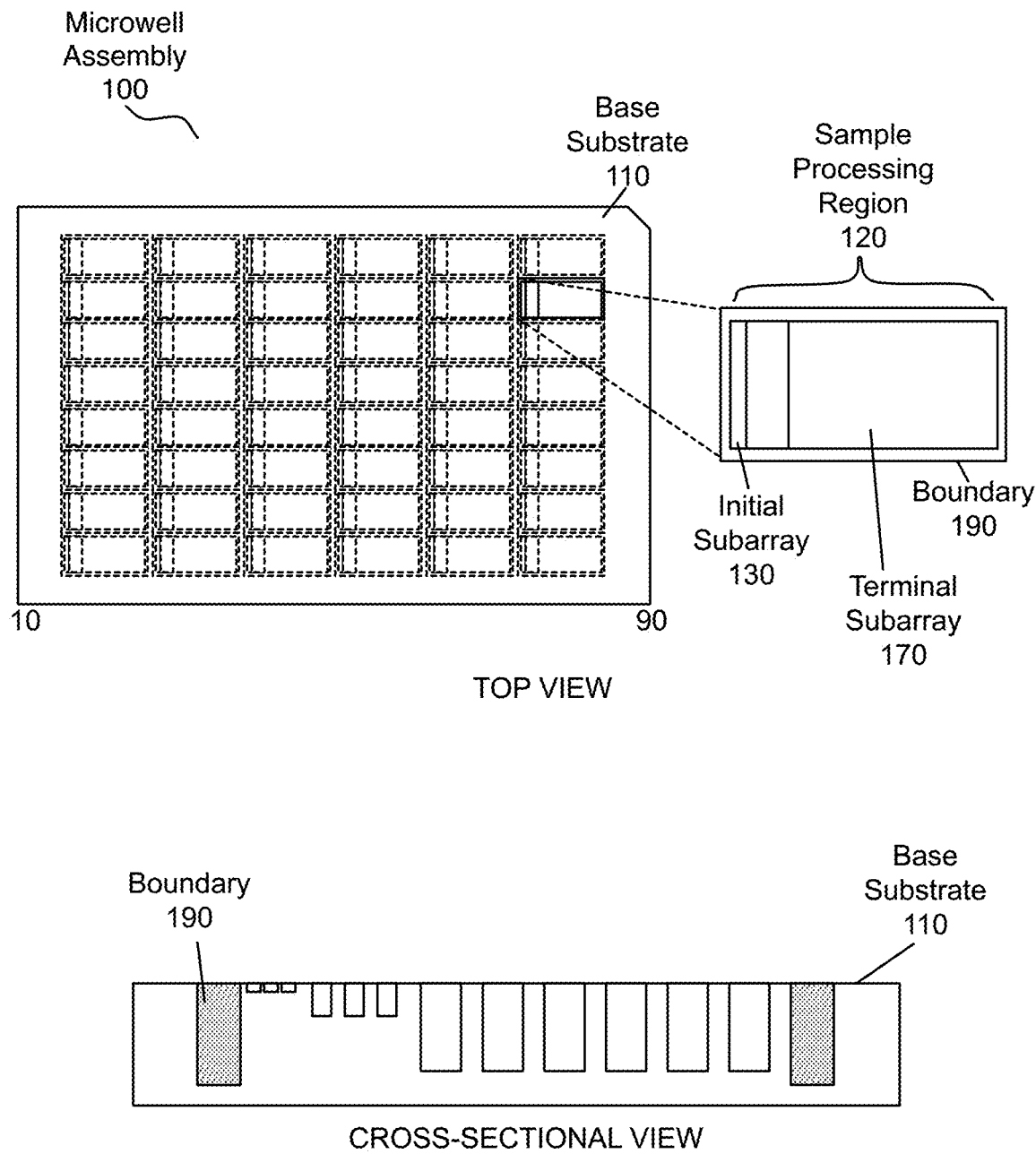
FIGS. 1A-1B depict schematic representations of embodiments of a microwell assembly for target detection and sample processing.

The following description of the preferred embodiments of the invention is not intended to limit the invention to these preferred embodiments, but rather to enable any person skilled in the art to make and use this invention.

1. BENEFITS

The invention(s) can confer several benefits over conventional systems and methods.

In particular, the invention(s) confer(s) the benefit of providing innovative solutions for target detection assays involving sample partitioning (e.g., for most probable number (MPN) applications, for digital PCR applications, for qPCR applications, for RT-PCR applications). The invention(s) also include innovative designs of sample processing disposables, such that multiple samples can be processed in parallel in a high-throughput manner that is not cost prohibitive in various industries. Such designs optionally include structures and features that function to provide automated sample application, controlled liquid spreading, controlled filling of the partitions (or microwells), controlled sample containment, the prevention of air bubble trapping during the filling of the partitions, the prevention of air bubble generation during sample containment, variable volume sample partitioning, humidity control, evaporation prevention, and/or cross-talk prevention, as described in more detail below.

By providing partitioning of samples in parallel, the invention(s) can also reduce impact of subsampling errors, thereby obviating use of subsampling correction factors (e.g., as a component of Poisson error correction factors) associated with detection of results from partitioned sample material.

The invention(s) also confer(s) the benefit of achieving high dynamic range with a relatively small number of partitions using disposables with collectively reduced footprint area, thereby contributing to a reduction in system and chip consumable size whilst maximizing sample throughput during sample processing.

The invention(s) also confer(s) the benefit of providing rapid processing to achieve PCR results in significantly reduced durations of time (e.g., 20-30 minutes for end-point PCR).

The invention(s) also confer(s) the benefit of providing disposables and system platforms that enable multiplexed processing of samples in parallel and an ability to simultaneously perform multiple assays (e.g., over 10 assays) per sample.

The invention(s) also confer(s) the benefit of providing systems and methods for target detection in a manner that significantly reduces human error, complexity of workflows, inherent assay variability, and duration of time needed for characterization and enumeration of targets.

The invention(s) also confer(s) the benefit of automating and/or simplifying processing steps, and in some variations, can automatically partition samples (e.g., samples less than or equal to 20 µl in volume, samples greater than 20 µl in volume) for various assays. By processing small volumes efficiently, the invention(s) can also significantly reduce waste associated with assay performance, and optimize run success and consistency across runs. Small volumes also significantly reduce the time required for reactions to achieve detection thresholds, thereby significantly reducing the time to result.

The invention(s) also confer(s) the benefit of mitigating inhibition issues associated with various reactions producing detectable signals by colorimetric and/or fluorescent (e.g., multi-channel fluorescent) methods.

The invention(s) also confer(s) the benefit of acquiring and integrating real-time fluorescence generated during the amplification reaction. The real-time amplification curves that result can provide information to distinguish between specific and non-specific amplification. Furthermore, when the Ct (or Cq) calculated from the real-time signal integration is evident at thermal cycles prior to that programmed for end-point reading, the time to result can be significantly reduced. As such, the invention(s) can include methods for shortening durations of time for returning results, and/or provision of real-time results.

The invention(s) also confer(s) the benefit of acquiring and integrating real-time fluorescence changes (e.g., decreasing fluorescence) during denaturation and melting reactions. The real-time melt curves that result can provide information regarding the target and sequence (and/or fragments thereof) that was amplified. This assay identification based on melt-curve analysis further expands the assay multiplexing capabilities provided by the invention(s).

The invention(s) also confer(s) the benefit of being compatible with the full array of molecular biology reagents required for amplification and denaturation reactions including optimal level of non-ionic detergents often used in storage buffers and exponential amplification reactions.

The inventions also cover automated image analysis of partitions (e.g., microwells) of sample processing arrays in parallel, using real-time amplification in different sized partitions, in individual partitions, and in combinations of partitions of same sizes and/or different sizes to predict the load/quantitation of target nucleic acid in the sample as early as possible (e.g., as described with respect to providing results with suitable confidence prior to end-point analyses). The invention(s) also covers the automated image analysis of a sample that has been partitioned into wells of different sizes, and automated analysis of further sub-partitions provided by microsphere-enabled-amplification within individual microwells.

Variations of the invention(s) also confer(s) the benefit of providing kits, compositions, methods, and apparatuses for target detection and characterization in a cost-efficient and time-efficient manner.

Additionally, through software and workflow improvements, the inventions can minimize number of manual operations performed by a user, and provide relevant system status reports to ensure smooth operation and sample processing.

Additionally or alternatively, the system and/or method can confer any other suitable benefit.

2. MICROWELL PLATE

Figure 1B:
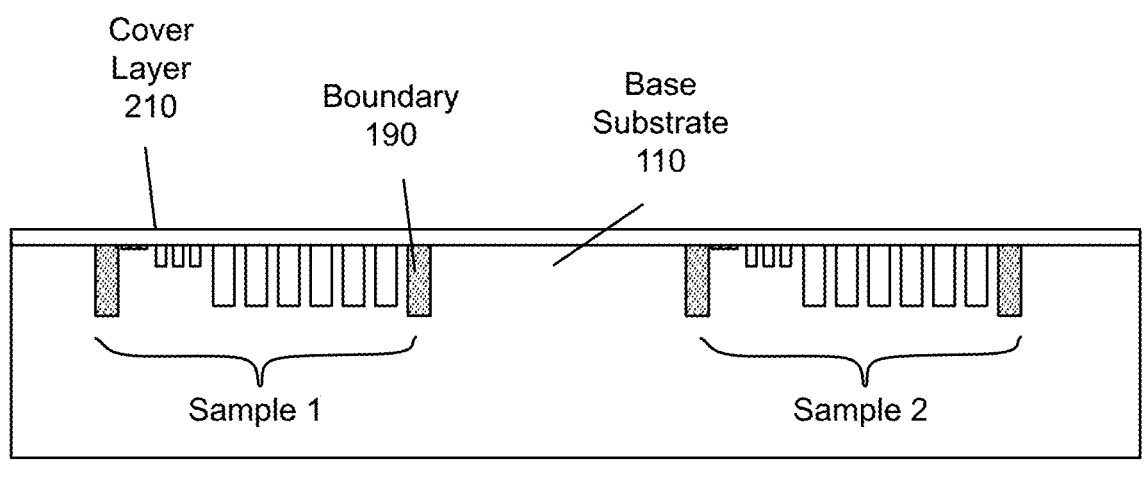

As shown in FIGS. 1A-1B, an embodiment of a microwell assembly 100 for target detection includes: a base substrate 110; and a set of sample processing regions (including sample processing region 120) defined at a broad surface of the substrate 110, wherein each of the set of sample processing regions includes: a set of microwell subarrays 130 arranged in a gradient (e.g., in volumetric capacity, in size, in surface area, in footprint, in cross-sectional area, etc.) between an upstream end 10 and a downstream end 90 of the sample processing region 120, and a boundary 190 separating the sample processing region 120 from adjacent sample processing regions. In relation to the gradient of microwell subarrays for each sample processing region, an initial microwell subarray 130 with wells having a first characteristic dimension (e.g., the smallest characteristic dimension) can be positioned at the upstream end 10 and a terminal microwell subarray 170 with wells having a second characteristic dimension (e.g., the largest characteristic dimension) can be positioned at the downstream end 90 of the sample processing region 120, with other variations described in more detail below. The set of sample processing regions 130 can be arranged as an array (e.g., two dimensional array), as described in more detail below, in order to provide functionality for multiplexed processing and detection, or performance of parallel sample processing in a redundant manner (e.g., to provide statistical confidence for various applications).

In some embodiments, as shown in FIG. 1B, the microwell assembly 100 can include a cover layer 210 configured to mate with the base substrate 110, the cover layer 210, where the cover layer 210 functions to promote spreading of samples across each of the set of sample processing regions 130 prior to sample processing and to maintain isolation of each of the set of samples individually during sample processing. The cover layer 210 can also be separated from the base substrate 110 by one or more functional layers, as described in more detail below.

The microwell assembly 100 functions to provide mechanisms for rapid sample distribution and processing, with high dynamic range of detection, in a low-cost manner. In particular, the microwell assembly can provide mechanisms for efficient distribution a sample across a set of partitions structured to automatically generate different dilutions of the sample using microwells arranged in gradients (e.g., in volumetric capacity, in size, in surface area, in footprint, in cross-sectional area, etc.). During use, an entity (e.g., human entity, automated system, etc.) can deliver samples to the microwell assembly, and with limited manual intervention (e.g., application of a cover layer 210), prepare the samples across partitions for processing.

The microwell assembly 100 has specific applications in PCR-applications involving small volumes (e.g., digital PCR, qPCR, etc.), and/or most probable number (MPN) determination. In particular, the microwell assembly 110 can receive a sample volume and distribute it across multiple subarrays of microwells, each subarray having a characteristic dimension, thereby facilitating rapid performance of sample partitioning and serial dilution operations, across multiple samples in parallel, to detect and characterize target microorganisms in a sample. The microwell assembly 100 can also include structures that prevent cross-talk between different samples being processed. Additional functions of the microwell assembly 100 are described in further detail below with respect to individual elements of the microwell assembly 110.

In embodiments, sample material processed by the microwell assembly can include biological samples including or derived from, for example, blood (e.g., whole blood, plasma, processed blood, blood lysate), saliva, mucus, sweat, interstitial fluid, synovial fluid, cerebral-spinal fluid, urine, bile, gastric fluids, biological waste, other biological fluids; tissues (e.g., homogenized tissue samples); food samples; liquid consumable samples; and/or other sample materials.

In embodiments, target material partitioned for processing using the microwell assembly 100 can include or be derived from one or more of nucleic acids (e.g., DNA, RNA, miRNA, etc.), proteins, amino acids, peptides, small molecules, single analytes, multianalytes, chemicals, and/or other target material, in order to enable genomic, proteomic, and/or other multi-omic characterization of single cells for various applications.

2.1 Base Substrate and Sample Processing Regions with Microwell Subarrays

2.1.1 Base Substrate

As shown in FIG. 1A, the microwell assembly 100 includes a base substrate 110 supporting a set of sample processing regions described in further detail below. The base substrate 110 thus functions to support a set of samples and to facilitate processes for detecting and characterizing target material from the set of samples with high dynamic range.

In material composition, the base substrate 110 can be composed of one or more of: a polymer (e.g., polypropylene, polydimethylsiloxane, polystyrene, polyvinyl chloride, polymethyl methacrylate, cyclic olefin copolymer, polycarbonate), a silicon-derived material, glass, a metallic material, a ceramic material, a natural material, a synthetic material, and/or any suitable material. In particular, material selection can be based upon one or more of: manufacturing considerations, surface properties desirable for sample processing, optical properties, bulk properties (e.g., in terms of density, etc.), surface properties, thermal properties, mechanical properties, and/or any other suitable properties. Furthermore, all parts of the base substrate 110 can be constructed using the same material(s), different materials (e.g., if each portion of the base substrate 110 has different design constraints), and/or any combination of materials. Furthermore, the base substrate 110 can be a unitary body, or a base substrate 110 having discrete portions that are coupled together (e.g., during manufacturing). The base substrate 110 containing the microwell arrays may be manufactured using techniques such as injection molding, compression injection molding, embossing, Lithographic etching, Laser etching, and/or other methods.

In relation to optical properties, the material(s) of the base substrate 110 can have any degree of transparency, reflectivity, or other optical characteristics. For instance, materials can be transparent to enable optical analysis, interrogation, or observation (e.g., from a bottom surface of the base substrate 110, from a top surface of the base substrate 110, etc.). Additionally or alternatively, portions of the base substrate 110 can be opaque, transparent, translucent, and/or any suitable opacity (e.g., to promote containment of detectable signals from each microwell and prevent signal interference, to reduce background and improve signal-to-noise ratios associated with optical detection, etc.). As such, variations of the materials and/or configurations can be configured to enable signal detection from individual microwells while promoting containment of detectable signals (e.g., in relation to containment of fluorescence, in relation to containment of other signal types) within individual microwells of the base substrate 110. Furthermore, variations of materials of the substrate can be configured and/or treated to prevent absorption of sample processing materials.

In relation to bulk properties, the material(s) of the base substrate 110 can be configured with a level of density or other bulk characteristic appropriate for sample processing. In variations, the base substrate 110 can be composed of or otherwise incorporate a polymer (e.g., polytetrafluoroethylene (PTFE), polyethylene (PE), polyvinyl alcohol (PVA), etc.), a ceramic, or another suitable material (e.g., natural material, synthetic material) having suitable intrusion ratings (e.g., according to the IP scale, according to another rating scale) or particle retention characteristics (e.g., with rated retention of particles below 1 micron, with rated retention of particles greater than or equal to 1 micron).

In relation to surface properties, the material(s) of the base substrate 110 can be configured with desired hydrophilic/hydrophobic properties (e.g., a high degree of hydrophilicity) determined by, for instance, contact angle and wettability characteristics. In relation to other electrical and physical properties, the material(s) of the base substrate 110 can be configured with a desired charge (e.g., in relation to characteristics of sample fluids and/or sample processing fluids used), electric field characteristics, characteristics associated with mitigation of bubble formation and/or elimination of bubbles, conductivity, resistance, and/or any other suitable surface or physical characteristics. Specific areas of the substrate such as the microwells and moats may be rendered hydrophilic but the banks in between samples may be made hydrophobic. Additionally or alternatively, the material(s) of the base substrate 110 are preferably configured to be non-reactive with fluids, sample, and/or sample processing material used. Additionally, the base substrate 110 may be configured to release temperature conductive particles that aid in increasing the thermal uniformity of the reactants in the microwell. Additionally or alternatively, the material(s) of the base substrate 110 can be configured/structured to absorb inhibitors that inhibit materials associated with target detection. For example, the material of base substrate 110 can be configured to absorb or otherwise bind RNAses/DNases, proteinases added to the reaction to digest biological material during sample prep, and/or any biological lysate from the sample prep that may inhibit the target detection reaction. Additionally or alternatively, the material of base substrate 110 can be configured to be resistant to acidic or basic pHs of the reaction mixture. Additionally, the material of the base substrate 110 may be configured to absorb materials such as primer-dimers that tend to obfuscate the true fluorescence signal generated by the target amplification products. Additionally or alternatively the surface of the base substrate 110 exposed to receiving fluid may have desired surface finish.

In relation to thermal properties, the material(s) of the base substrate 110 can be configured with desired thermal properties, with respect to heat transfer and/or heat retention characteristics (e.g., in the context of thermocycling). In particular, the base substrate 110 can be configured with desired thermal conductivity (e.g., greater than 4 W/m*K, etc.) and/or heat capacity characteristics (e.g., as appropriate to sample heating, cooling, and/or thermocycling steps). In some variations, the material(s) of the base substrate 110 can include embedded thermally conductive particles to provide thermal conductivity characteristics. In one variation, the base substrate 110 can be configured with thermal properties such that it can efficiently transfer heat to and/or away from fluids contacting the base substrate 110. For instance, in variations where the base substrate 110 is coupled to a heating or cooling element (e.g., directly, indirectly through cover layer 210, indirectly through film layers, etc.), the base substrate 110 can be configured to facilitate transfer of heat to contents of the microwells during incubation and/or transfer of heat away from the fluids. However, the base substrate 110 can have other suitable thermal properties based on application of use. For instance, the base substrate 110 can be configured with low thermal conductivity (e.g., as an insulative material), such that the material does not significantly affect temperatures of the fluids it contacts during operation.

In relation to mechanical properties, material(s) of the base substrate 110 can be configured with desired mechanical properties, including one or more of: stiffness, strength, elastic behavior, hardness, and other properties. Additionally or alternatively, the base substrate can be configured to be compatible with automated plate arm robotic subsystems, with respect to robustness during handling by automated systems, in relation to gripping of the base substrate 110, compressing the base substrate 110, applying shear forces to the base substrate 110, and/or applying any other suitable forces to the base substrate 110.

In dimensions, the base substrate 110 can have the format of an SBS microwell plate (e.g., 127.76 mm×85.48 mm footprint); however, the base substrate 110 can alternatively have other suitable dimensions and/or form factor. The plates of the microwell assembly may additionally or alternatively be designed to be easily stackable for packaging or for use during sample runs.

Additionally or alternatively, the base substrate 110 can be configured to be sterilizable (e.g., using an autoclave, using other sterilization methods, etc.).

Additionally or alternatively, the base substrate 110 can be configured to selectively bind products generated during the target detection reaction, in order to facilitate washing of waste products from partitions or retain target material at desired surfaces of the base substrate for real-time/downstream detection or products. In relation to binding of products, the base substrate 110 can thus include one or more surfaces (e.g., microwell surfaces, base surfaces, etc.) functionalized with capture probes (e.g., oligonucleotide-conjugated probes for capture of nucleic acid or protein/peptide targets). In such applications, the capture probes can be coupled to the surfaces of the base substrate 110 and/or other microwell assembly surfaces 100 with linker molecules, where the linker molecules extend the capture probes into space to interact with target sample material or sample products produced during sample processing. Additionally or alternatively, the linker molecules can be cleavable (e.g., by enzymatic cleaving mechanisms, by photocleaving mechanisms, by pH shift cleavage, by thermal cleaving mechanisms, by physical cleaving mechanisms, etc.).

2.1.2 Sample Processing Regions with Microwell Subarrays

As shown in FIG. 1A, the base substrate 110 defines a set of sample processing regions (including sample processing region 120), wherein each of the set of sample processing regions includes: a set of microwell subarrays 130 arranged in a gradient (e.g., in volumetric capacity, in size, in surface area, in footprint, in cross-sectional area, etc.) between an upstream end 10 and a downstream end 90 of the sample processing region 120. The set of sample processing regions functions to receive a set of samples and to facilitate distribution of the set of samples across a set of microwell subarrays, in order to enable performance of various assays (e.g., involving detection of targets using small volumes, such as in digital PCR, such as in qPCR, such as in digital LAMP, such as in qLAMP, etc.), serial dilution tests for each sample, and/or other processes for detection of one or more targets. In some variations, the set of sample processing regions can be configured to store dried or lyophilized sample processing materials (e.g., master mix, probes, primers, PCR enhancers, media, materials for PCR-associated assays, etc.) prior to receiving samples, in order to increase efficiency of sample processing. In some variations, the set of sample processing regions can be configured to be hydrophilic, hydrated, treated, and/or blocked with a non-specific absorption agent.

Figure 2:
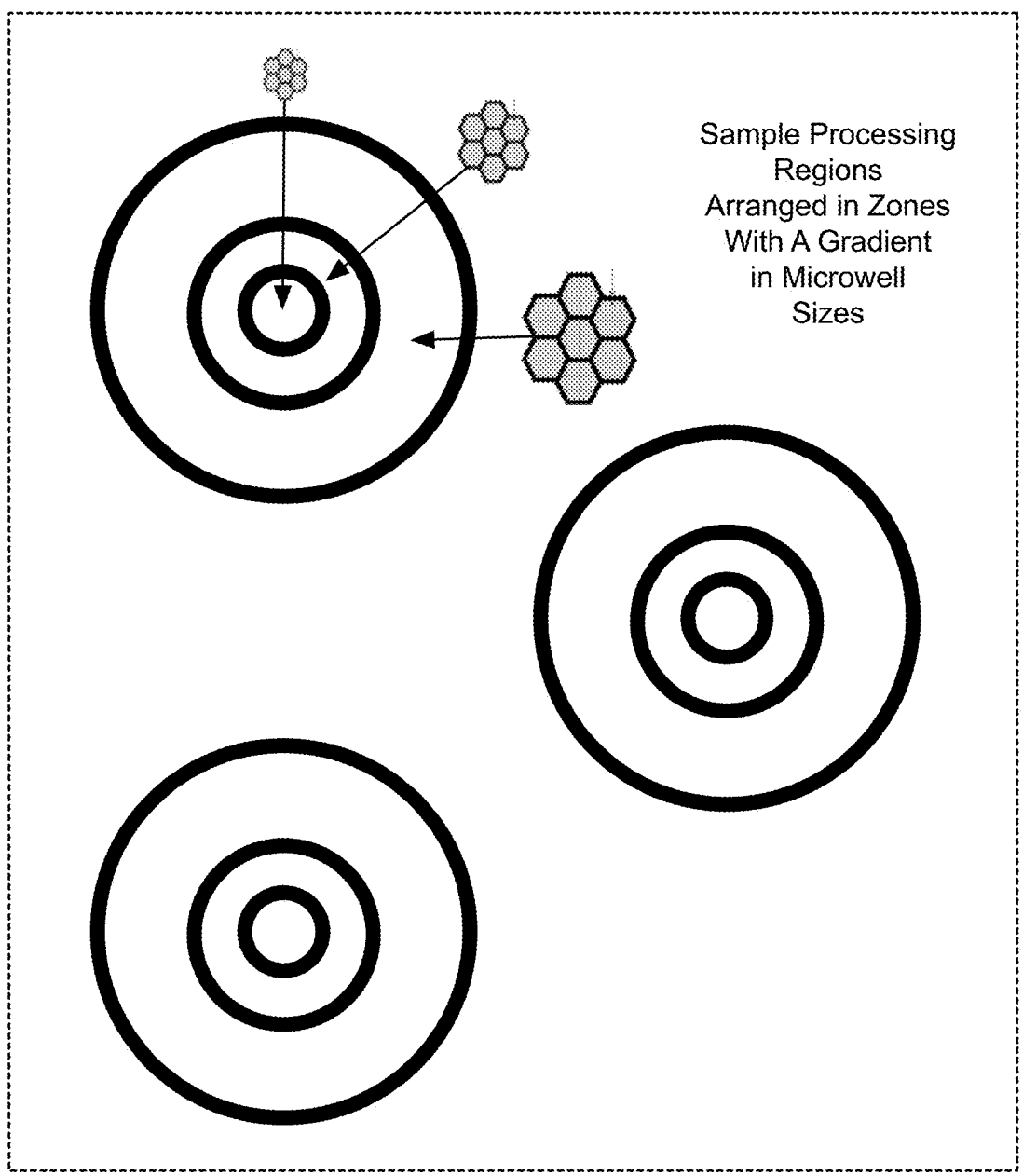
FIG. 2 depicts schematic representations of a variation of a microwell assembly for target detection.

In variations, the set of sample processing regions can be arranged as an array (e.g., rectangular array, other array, etc.) defined within the broad surface of the base substrate 110, where each region is configured to receive a separate sample (or separate aliquots of the same sample), such that the samples can be processed in parallel in a high-throughput manner. In embodiments where the broad surface of the base substrate 110 has a long axis and a short axis, the set of sample processing regions can be arranged in a rectangular array (e.g., 2D array) aligned with the long axis and the short axis (e.g., in relation to the number and configuration of samples for testing and/or number of microwell sizes desired). However, the set of sample processing regions can alternatively be arranged relative to another suitable axis. Furthermore, the set of sample processing regions may not be arranged in an array. For instance, in another variation shown in FIG. 2, each of the set of sample processing regions can be defined as a zone (e.g., circular zone, ellipsoid zone, polygonal zone, amorphous zone, etc.), and the microwell subarrays can be arranged along another suitable axis (e.g., radial axis, circumferential axis, etc.) or within another suitable coordinate system.

In variations, the number of sample processing regions included in the microwell assembly 100 can be governed by the dimensions of the base substrate 110 (with examples provided above), in relation to characteristic microwell dimensions and number of individual microwells desired for each microwell subarray, for various assays involving serial dilutions and/or detection of target material with high dynamic range.

In variations, microwell dimensions and number of microwells included in each of the set of sample processing regions can be optimized for providing suitable numbers of partitions and/or dilutions that enable detection of target material present at low concentration in a sample, such that the number and sizes of microwells provide the ability to detect such target material and return results with suitable statistical confidence.

In variations, microwell dimensions and number of microwells included in each of the set of sample processing regions can be optimized for MPN confidence limits in relation to number of partitions implemented and volume of each partition, in relation to sample volume received per region, for MPN determination.

Figure 3A:
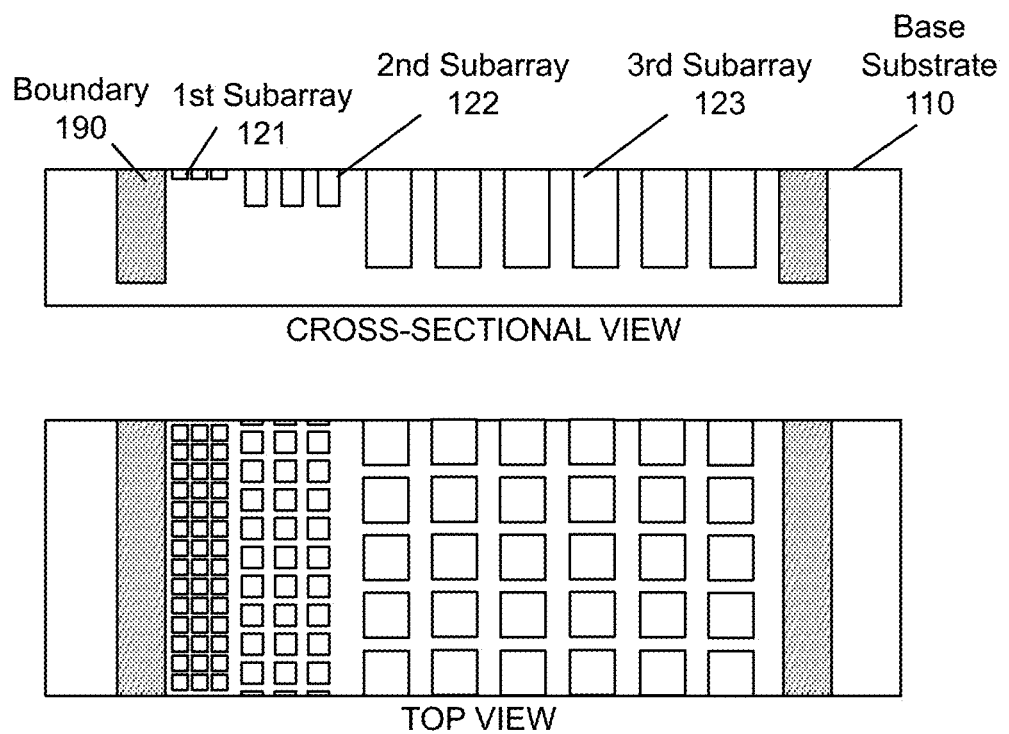
FIGS. 3A-3B depict schematic representations of a specific examples of a microwell assembly for target detection and sample processing.
Figure 3B:
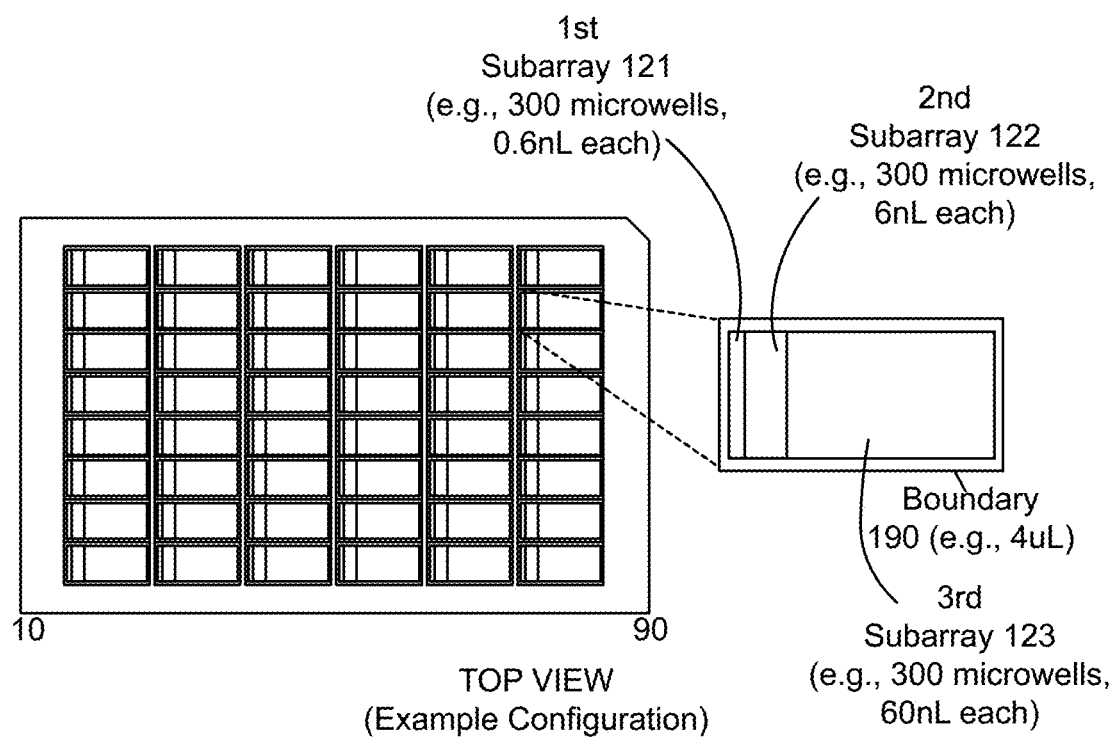

In examples (one of which is shown in FIGS. 3A and 3B), the set of sample processing regions can include between 2 and 96 sample processing regions. However, in other variations, the set of sample processing regions can include another suitable number of sample processing regions (e.g., less than 4 sample processing regions, more than 60 sample processing regions).

As described briefly above, each of the set of sample processing regions can include: a set of microwell subarrays 130 arranged in a gradient (e.g., in volumetric capacity, in size, in surface area, in footprint, in cross-sectional area, etc.) between an upstream end 10 and a downstream end 90 of the sample processing region 120, and a boundary 190 separating the sample processing region 120 from adjacent sample processing regions. The set of microwell subarrays 130 functions to provide, for each sample being processed, a set of partitions with a known distribution of volumes for performing quantification of target material characteristics from a sample, determinations of MPN and/or other assays for target detection (e.g., using digital PCR, using qPCR, etc.) from a sample. Each of the set of microwell subarrays can thus have partitions (e.g., microwells) having a different characteristic volume for each of the partitions, in order to provide a suitable number of dilutions and partitions per dilution to generate minimum and maximum detectable values (e.g., counts, concentrations, MPN values) with suitable confidence limits. However, each of the set of the set of microwell subarrays 130 can have a different characteristic (e.g., size, surface area, footprint, cross-section transverse to a longitudinal axis, cross-section parallel to a longitudinal axis, other cross-section, etc.).

In variations, a sample processing region of the base substrate 110 can include between 2 and 10 microwell subarrays, each of the set of microwell subarrays having from 10 through 100,000 partitions. Each sample processing region can accept between 1 μL and 100 μL of sample, in order to provide values (e.g., values related to detection of target material, counts, MPN values, etc.) between a minimum and maximum range of 5 to 10,000,000, with suitable confidence limits. Each microwell can have a volume from 0.1 nL to 100 nL for digital PCR applications, qPCR applications, MPN applications, and/or other applications. However, a sample processing region can include other suitable numbers of microwell subarrays (e.g., less than 2 microwell subarrays, greater than 10 microwell subarrays), each having other suitable numbers of partitions (e.g., less than 10 partitions, greater than 100,000 partitions, greater than 500,000 partitions), in order to accept other sizes of sample volumes (e.g., less than 0.1 nL, greater than or equal to 100 nL, etc.) for enabling determination of target values within another suitable range. In a specific example, each sample processing region can produce a large dynamic range of 6 logs in the context of MPN, or alternatively, 9 logs for qPCR; however, variations can produce another dynamic range depending upon number of microwell subarrays, and microwell configuration for each microwell subarray.

In particular, the number of microwell subarrays/characteristic volumes, and number of partitions per microwell subarray can be configured in association with determination of the solution for λ in expression [1] below, where exp(x) is $e^x$, K denotes the number of dilutions, $g_j$ denotes the number of positive partitions (e.g., due to growth, due to amplification of target material, etc.) in the jth dilution, $m_j$ denotes the amount of the original sample put in each partitions in the jth dilution, and $t_j$ denotes the number of partitions in the jth dilution.

$$\sum_{j=1}^{k} \frac{g_j m_j}{1 - \exp(-\lambda m_j)} = \sum_{j=1}^{k} t_j m_j \quad [1]$$

In a specific example, shown in FIG. 3A, each of the set of sample processing regions can have three microwell subarrays distributed in a gradient along a longitudinal axis of the sample processing region, where a first microwell subarray 121 has a characteristic volume of 0.6 nL per partition and 300 microwell partitions for a total volume of 0.18 uL. As shown in FIG. 3A, each microwell of the first microwell subarray 121 can have a 0.09 mm side length, a 0.074 mm height, an area of 0.0081 mm$^2$, and ribs of 0.1 mm width separating each microwell from adjacent microwells. The sample processing region can also include a second microwell subarray 122 that has a characteristic volume of 6 nL per partition and 300 microwell partitions for a total volume of 1.8 uL where, as shown in FIG. 3A, each microwell of the second microwell subarray 122 can have a 0.15 mm side length, a 0.267 mm height, an area of 0.0225 mm$^2$, and ribs of 0.18 mm width separating each microwell from adjacent microwells. The sample processing region can also include a third microwell subarray 123 that has a characteristic volume of 60 nL per partition and 300 microwell partitions for a total volume of 18 uL where, as shown in FIG. 3A, each microwell of the third microwell subarray 123 can have a 0.3 mm side length, a 0.667 mm height, an area of 0.09 mm$^2$, and ribs of 0.21 mm width separating each microwell from adjacent microwells. The microwells can have a suitable pitch to facilitate distribution of sample fluid across the microwell subarrays. Such a configuration can enable each sample processing region to process an ~20 uL sample for applications, as discussed. However, variations of the specific example shown in FIG. 3A can alternatively include different volumetric capacities per partition type, numbers of partitions per microwell subarray, different dimensions, and/or different ribs for separation of adjacent microwells.

As shown in FIG. 3B, the sample processing regions associated with units of the sample processing region shown in FIG. 3A can be arranged in a rectangular array, where the rectangular array includes 8 rows and 6 columns of sample processing regions for a total of 48 sample processing regions, thereby enabling processing of 48 samples. However, in variations of the specific example, the set of sample processing regions can include another suitable number of sample processing regions arranged in any suitable configuration.

In variations, a cross section of each microwell can be polygonal (e.g., hexagonal, rectangular, etc.) or non-polygonal (e.g., circular, ellipsoidal, amorphous, etc.) in cross-section (e.g., a cross-section taken across a plane parallel to the broad surface of the base substrate 110). Additionally or alternatively, a cross section of each microwell can be tapered along a direction away from the broad surface of the substrate 110 toward the base of each microwell. As such, each well can have an opening at the broad surface of the base substrate 110, such, that sub-volumes of a sample can enter the microwells from a direction perpendicular to the broad surface of the base substrate 110. However, the opening(s) of the microwells can be configured in another suitable manner. Furthermore, the microwells can be arranged in a packed configuration (e.g., hexagonal close packed, rectangular close packed, other close packed configuration, etc.) or non-packed configuration.

In relation to the gradient of microwell subarrays for each sample processing region, an initial microwell subarray 130 with wells having a first characteristic dimension (e.g., the smallest characteristic dimension) can be positioned at an upstream end 10 of the sample processing region, and a terminal microwell subarray 170 with wells having a second characteristic dimension (e.g., the largest characteristic dimension) can be positioned at a downstream end 90 of the sample processing region 120. As such, the microwell subarrays can have larger and larger characteristic microwell dimensions in an upstream to downstream direction. Alternatively, the microwell subarrays can have smaller and smaller characteristic microwell dimensions in an upstream to downstream direction. Still alternatively, the microwell arrays may be organized in a gradient or non-gradient in another suitable manner (e.g., along another directional axis, in relation to another microwell characteristic). Still alternatively, each sample processing region can be otherwise configured (e.g., with stepwise increments across the gradient of microwells) in other variations. For instance, well dimensions may not be organized with a gradient in an upstream to downstream direction or in a downstream to upstream direction, but rather in a lateral direction (e.g., orthogonal to the upstream to downstream direction) or other direction.

As shown in FIGS. 3A and 3B, the base substrate 110 can include a set of boundaries (including boundary 190) separating each sample processing region from adjacent sample processing regions, thereby functioning to prevent sample cross-talk. The boundary 190 can be configured as a recess (e.g., as a moat), or as a protrusion, or can alternatively include recessed and protruding portions. The boundary 190 can also be configured as a region configured to promote evaporation or absorption of sample overflow, whereby, upon entry of sample into the region, the sample evaporates and/or is absorbed to the walls of the boundary 190. In variations wherein the boundary 190 is defined as a recessed perimeter about a sample processing region, the boundary 190 can function as a moat into which sample overflow can be received during sample processing. Alternatively, the boundary 190 can serve another suitable purpose.

In the specific example, as shown in FIGS. 3A and 3B, each sample processing region can be surrounded by a boundary 190, which can accept approximately 4 uL of overflow (e.g., of sample, of sample processing solution, etc.). However, variations of the boundary can accept other volumes of fluid and/or be configured in another suitable manner. In other embodiments, the boundaries 190 of one or more of the sample processing regions can be connected, provided that the microwells of each sample processing region are not otherwise in communication with microwells of other sample processing regions.

Additionally or alternatively, the boundary 190 can be composed of an absorbent material configured to receive and soak up overflowing material from the sample processing regions.

Additionally or alternatively, the boundary or boundaries can include one or more outlets (e.g., to a waste chamber), away from the sample processing regions, such that overflowing material can be delivered away from the sample processing regions and prevent re-entry into the sample processing regions.

Furthermore, while the base substrate 110 can be physically contiguous, in variations, the base substrate 110 can be configured to be separatable between adjacent sample processing regions (e.g., with perforations, with reversibly locking components, etc.) in order to provide individual downstream processing and/or analysis of each sample processing region. However, the base substrate 110 can alternatively be configured to be non-separatable.

While embodiments, variations, and examples of the microwells of the sample processing region are described above, aspects of the microwells and/or sample processing regions can be adapted from one or more of: U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; U.S. application Ser. No. 15/815,532, filed 16 Nov. 2017; U.S. application Ser. No. 16/115,370, filed 28 Aug. 2018, U.S. application Ser. No. 16/564,375, filed 9 Sep. 2019, and U.S. application Ser. No. 16/816,817, filed 12 Mar. 2020, which are each incorporated in their entirety by this reference.

2.2 Cover Layer and Optional Elements 2.2.1 Cover Layer

Figure 4:
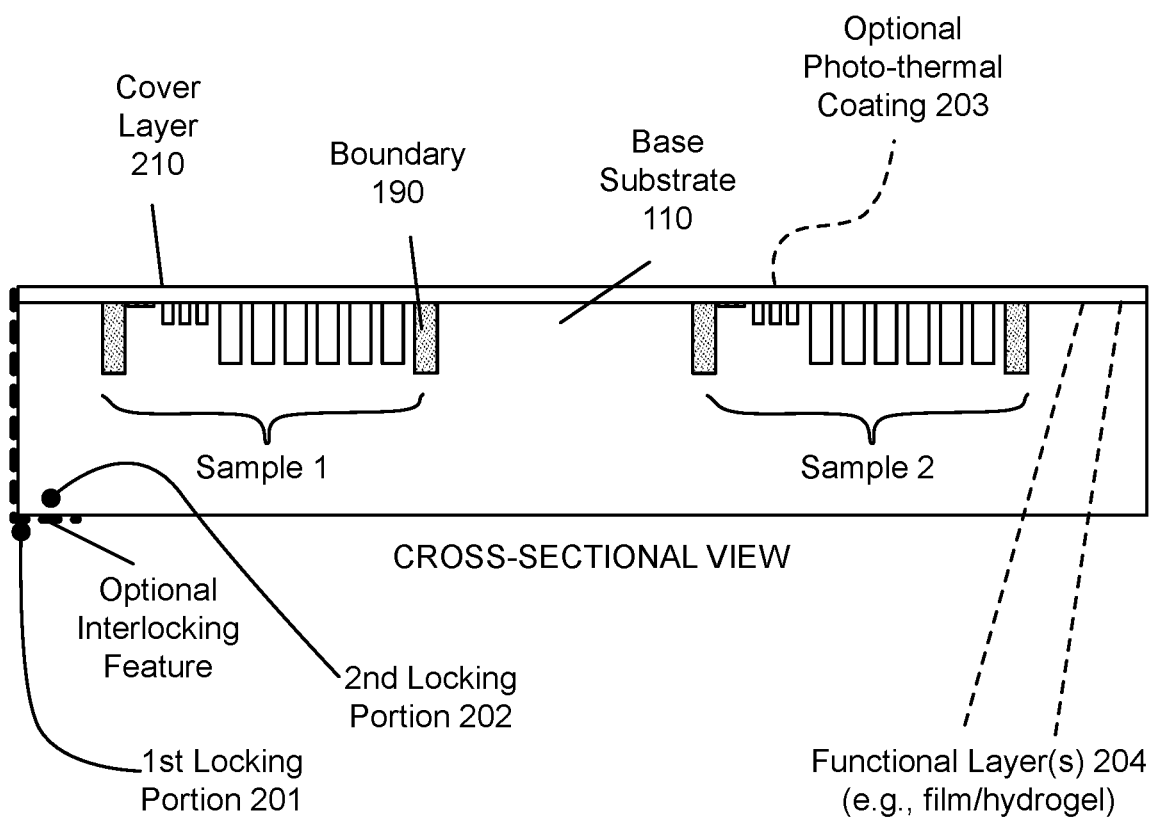
FIG. 4 depicts a side view of a microwell assembly, with a cover component, for target detection and sample processing by way of a heater.

As shown in FIGS. 1B and 4, in some embodiments, the microwell assembly 100 can include a cover layer 210 configured to interface with the base substrate 110. The cover layer 210 functions to spread, seal and/or isolate samples being processed at the base substrate 110 and to facilitate heat transfer from a heating element (described in more detail below) to samples at the base substrate. In operation, processing components (e.g., heating elements, disposable moving elements, etc.) of the platform described in more detail below can be configured to bias or otherwise press the cover layer 210 against the base substrate 110 during one or more stages of sample processing, in order to isolate samples prior to subsequent sample processing steps, while preventing sample cross-contamination.

In material composition, the cover layer 210 can be composed of one or more of: a polymer (e.g., polypropylene, polydimethylsiloxane, polystyrene, polyvinyl chloride, polymethyl methacrylate, cyclic olefin copolymer, polycarbonate), a silicon-derived material, glass, a metallic material, a ceramic material, a natural material, a synthetic material, and/or any suitable material. In particular, material selection can be based upon one or more of: manufacturing considerations, surface properties desirable for sample processing, optical properties, thermal properties, mechanical properties (e.g., compressibility, stiffness, tensile strength), bulk properties (e.g., in terms of density, etc.), surface properties, and/or any other suitable properties. Furthermore, all parts of the cover layer 210 can be constructed using the same material(s), different materials (e.g., if each portion of the cover layer 210 has different design constraints), and/or any combination of materials. Furthermore, the base substrate 110 can be a unitary body, or a base substrate 110 having discrete portions that are coupled together (e.g., during manufacturing).

In relation to thermal properties, the material(s) of the cover layer 210 can be configured with desired thermal properties, with respect to heat transfer and/or heat retention characteristics. In particular, the cover layer 210 can be configured with desired thermal conductivity (e.g., greater than 3 W/m*K, etc.) and/or heat capacity characteristics (e.g., as appropriate to sample heating and/or thermocycling steps in the context of PCR operations). In one variation, the cover layer 210 can be configured with thermal properties such that it can efficiently transfer heat to or away from the microwell assembly 100 during sample processing and/or thermocycling. Furthermore, in some embodiments, the cover layer 210 can be composed of a material that bonds to the base substrate 110 upon being heated by an external element (e.g., of platform 300) described in more detail below. Bonding can be performed without entirely melting or otherwise structurally compromising the cover layer 210. Additionally or alternatively, the cover layer 210 can include a distribution of thermally-conductive particles to promote heat transfer.

In relation to mechanical properties, material(s) of the cover layer 210 can be configured with desired mechanical properties, including one or more of: stiffness, strength, elastic behavior, hardness, and other properties. For instance, variations of the cover layer 210 can be composed of an elastomeric material that can be elastically deformed, where reversible deformation of the elastomeric cover layer 210 can enable operation modes that facilitate sample handling and/or prevent bubble formation/mitigate effects of bubbles.

In examples in which the cover layer 210 is elastomeric, the cover layer 210 can be composed of or otherwise include an elastomer (e.g., silicone, polyether/polyamide material, polyurethane material, polyester material, etc.), where the elastomer can be processed to include reinforcement carriers, thermally conductive components (e.g., Carbon, Copper, Aluminum, Aluminum Nirtride, Boron Nitride, Silver particles), or other suitable elements. However, the cover layer 210 can be composed of other suitable materials (e.g., microporous polycarbonate, cellulose acetate, nitrocellulose, glass fiber, microporous nylon, polytetrafluoroethylene, regenerated cellulose, polyvinyl fluoride, polypropylene, microporous polyester, polyvinylidene fluoride, re-probing charged nylon, etc.)

The cover layer 210 can additionally or alternatively include venting channels to prevent bubble formation, remove formed bubbles/mitigate effects of bubbles.

In relation to bulk properties, material(s) of the cover layer 210 can be configured with a level of density or other bulk characteristic appropriate for sample processing and/or incubation purposes. In variations, the cover layer 210 can be composed of or otherwise incorporate a polymer (e.g., polytetrafluoroethylene (PTFE), polyethylene (PE), polyvinyl alcohol (PVA), etc.), a ceramic, or another suitable material (e.g., natural material, synthetic material).

In relation to surface properties, the material(s) of the cover layer 210 can be configured with desired hydrophilic/hydrophobic properties (e.g., a high degree of hydrophobicity) determined by, for instance, contact angle and wettability characteristics. In relation to other electrical and physical properties, the material(s) of the cover layer 210 can be configured with a desired charge (e.g., in relation to characteristics of sample fluids and/or sample processing fluids used), electric field characteristics, conductivity, resistance, and/or any other suitable surface or physical characteristics. Additionally or alternatively, the material(s) of the cover layer 210 are preferably configured to be non-reactive with fluids used during sample processing.

In relation to optical properties, the material(s) of the cover layer 210 can have any degree of transparency, reflectivity, or other optical characteristics. For instance, materials can be transparent to enable optical analysis, interrogation, or observation (e.g., from a top surface of the cover layer 210, etc.), but can be opaque, transparent, translucent, and/or any suitable opacity.

In variations, the surface of the cover layer 210 facing the microwells of the base substrate 110 may also be of smoothness less than few microns (e.g., a surface roughness less than 20 microns, a surface roughness less than 10 microns, a surface roughness less than 5 microns, a surface roughness greater than 20 microns, etc.), such that biasing of the cover layer 210 against the microwells, provides suitable sealing against the top surface of the microwells but minimal intrusion of elastomeric material (e.g., less than 5 microns) into the microwell reactors.

The surface of the cover layer 210 facing the microwells of the base substrate 110 may also be optically reflective (e.g., reflective toward interior volumes of the set of sample processing regions) to increase the fluorescence signal delivered from the reaction vessels into a camera/sensor (e.g., fluorescence camera). The cover layer 210 (e.g., surface facing the microwells) may also be coated with a IR-absorptive surface such that the temperature of the top of the microwells may be optically interrogated from a distance using an IR-imaging camera. The surface of the cover layer 210 facing the microwells may also be coated with a photo-thermal coating 203 (shown in FIG. 4) such that the light of specific wavelength and intensity could be used to thermally activate the surface to provide temperature incubations within the microwells (e.g., the cover layer has a component structured to transmit heat to contents of the set of sample processing regions upon activation by light characterized by a wavelength range, using a photothermal mechanism).

The surface of the cover layer 210 facing the microwells of the base substrate 110 may also be coated with an inductive coating such that a heating element/electrical element (e.g., an induction coil" may cause controlled eddy-current-based joule heating of the microwells. The surface of the cover layer 210 facing the microwells may also be coated with a metal coating such that RF microwaves can cause controlled microwave heating of the microwells.

As such, the cover layer 210 can be configured to support controlled heating mechanisms for heating and/or cooling of microwell contents, in response to activation by one or more stimuli.

In a specific example, the cover layer 210 comprises an elastomer composed of silicone with a fiberglass reinforcement carrier, a thermal conductivity greater than 3 W/m*K, a thickness from 25-200 microns, an operating temperature range from −60-230 C, a Shore hardness from 10-70, a heat capacity from 0.5-5 J/g-K, a density from 1-5 g/cc, and a Young's modulus from 20-60 kPa. However, variations of the specific example of the cover layer 210 can be composed of another suitable material with other suitable properties.

In forming an assembly, the cover layer 210 can mate with the base substrate 110 by inclusion of coupling or interlocking features. For instance, the cover layer 210 can be configured to bond (e.g., by way of an adhesive, by way of thermal bonding, etc.) to the base substrate 110 during operation. Additionally or alternatively, the cover layer 210 can include a lip or a set of tabs that engage a surface (e.g., bottom surface, peripheral surface) of the base substrate 110, thereby providing coupling between the base substrate 110 and the cover layer 210. In other variations, coupling can be provided with another suitable mechanism (e.g., press fit mechanism, snap fit mechanism, magnetic mechanism, adhesive mechanism, gravity mechanism, etc.). As such, the cover layer 210 can include a first locking portion 201 complementary to a second locking portion 202 of the base substrate no (as shown in FIG. 4). Coupling between the base substrate no and the cover layer 210 can be reversible or otherwise permanent. In still other variations, the cover layer 210 may not be configured to couple with the base substrate no.

In still other variations, the cover layer 210 may contact the base substrate 110 in sequential or vectorial fashion (e.g., in a controlled manner from one end of the base substrate 110 to another end of the base substrate 110) such that each sample is sealed in sequence from one end to the other of a sample processing region. Sealing in this manner provides a means to create sealed partitions in a predetermined order or sequence (e.g., with larger microwells being filled prior to smaller microwells, with smaller microwells being filled prior to larger microwells, etc.).

The cover layer 210 can also be configured to irreversibly seal the microwell partitions before, during and after amplification (e.g., by a PCR process), so as to prevent release and contamination of the environment with amplification products. The cover layer 210 can, however be configured to be accessed (e.g., punctured by a needle, accessed by an aspiration and delivery component, etc.) to extract amplification product for downstream genotyping or sequencing reactions by simple aspiration into a capillary.

2.2.2 Optional Elements

The cover layer 210 can also be separated from the base substrate no by one or more functional layers 204 (shown in FIG. 4). For instance, the cover layer 210 can be separated from the base substrate 110 by a film layer/or a hydrogel layer, in order to facilitate coupling between the cover layer 210 and the base substrate 110, provide further separation between adjacent sample processing regions to prevent sample cross talk, and/or to perform microwell sealing functions. Furthermore, the microwell assembly can include multiple membranes, in relation to design functionality and/or application of use of the system 100.

Furthermore, variations of the microwell assembly 100 can additionally or alternatively include or support other suitable elements (e.g., oil layers, other partitioning material layers, buoyant hydrophobic particles, temperature indicating particles, buoyant self-polymerizing material, biological membranes, cellular layers, biological coating, sample processing substrates included or bound to microwell surfaces, configuration media, dilution media, media provided in a lyophilized state, etc.) that facilitate sample processing and/or sample incubation, while facilitating gas exchange with the environment and preventing sample cross talk.

3. PLATFORM

Figure 5:
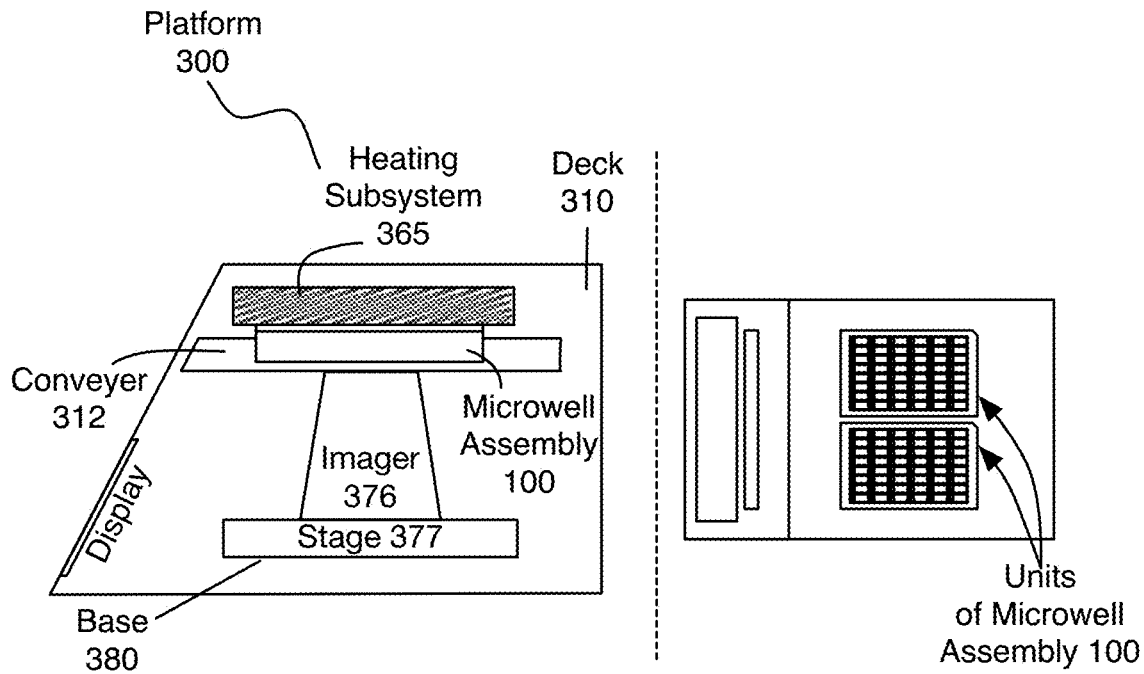
FIGS. 5 and 6 depict embodiments and views of a platform for automating processing of samples using units of a microwell assembly.
Figure 5:
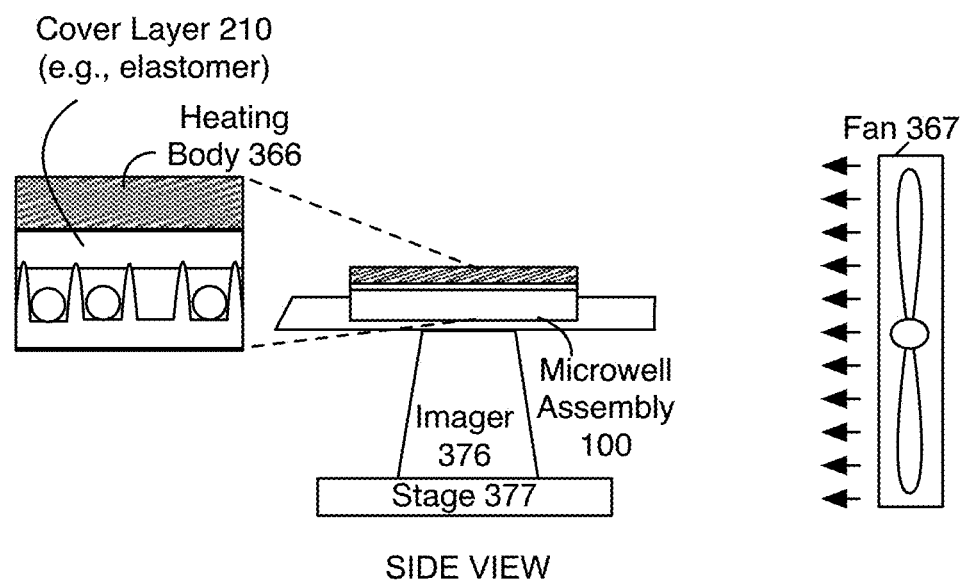
Figure 6:
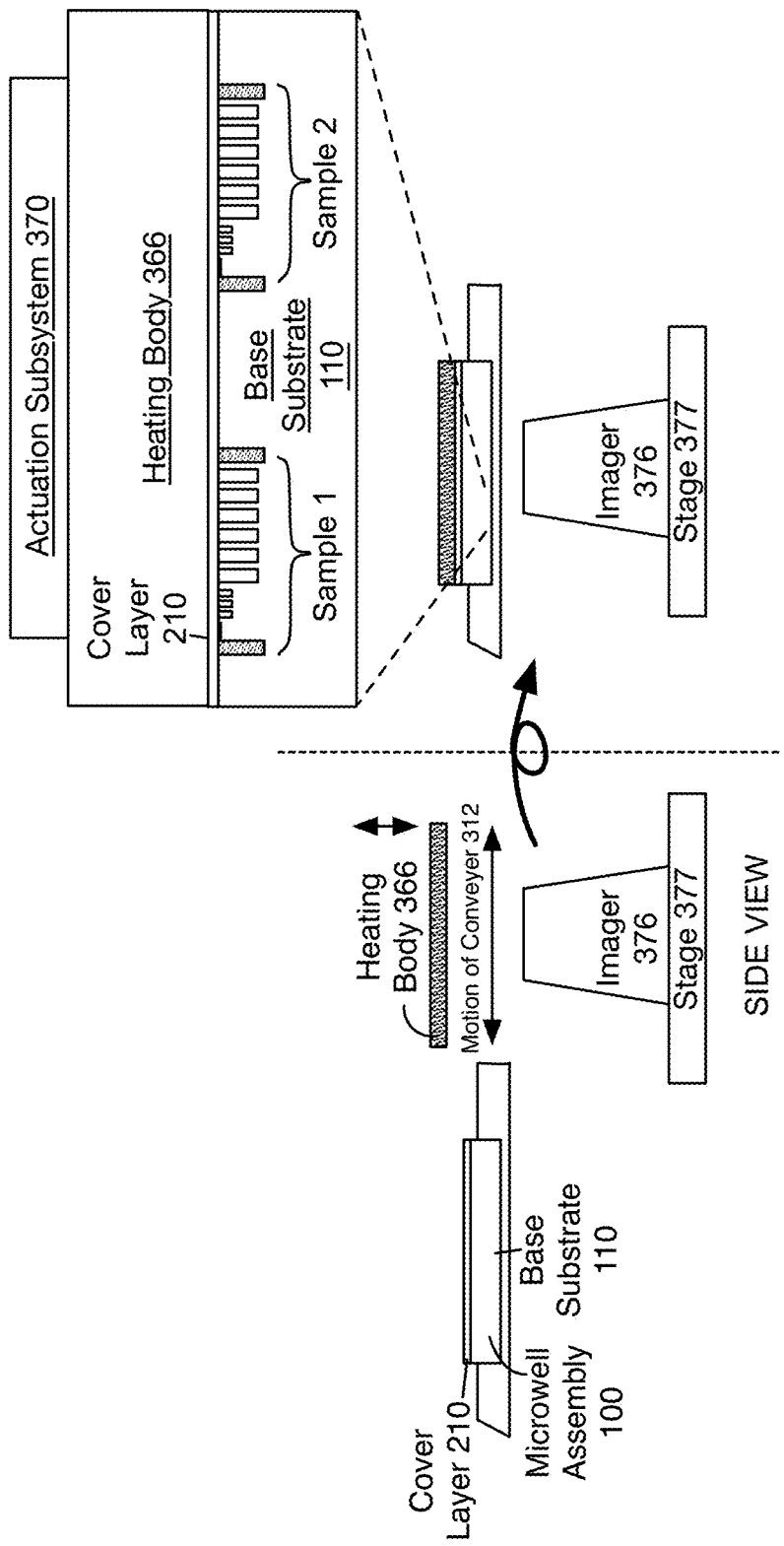

As shown in FIGS. 5 and 6, an embodiment of a platform 300 for automated sample processing (e.g., for processing samples using units of the microwell assembly 100 described above) includes: a deck 310 for receiving and positioning one or more units of the microwell assembly (e.g., with a conveying element); an actuation subsystem 370 (e.g., including a gantry) for actuating tools for interactions with the set of sample processing elements supported by the deck 310; and a base 380 supporting various processing subsystems (e.g., an imaging subsystem) and a control subsystems in communication with the processing subsystems, where the control subsystems control states of the deck 310, the set of sample processing elements, and the actuation subsystem 370 in order to transition the platform 300 between various operation modes. In examples, the platform 300 can provide functionality for loading samples in a high throughput manner and/or sample reading in a high throughput manner. Embodiments, variations, and examples of operation modes, which provide various workflows, are described in further detail in Section 4 below.

3.1. Deck and Deck-Supported Elements

As shown in FIGS. 5 and 6, the deck 310 functions as a platform to receive, support, and position one or more components for automated processing of samples using units of the microwell assembly 100 described above. Furthermore, the deck 310 can function to position (e.g., with a conveying element, with a sliding drawer, with rollers, with a robotic apparatus, etc.) one or more components to align with or otherwise interact with heating subsystems, imaging subsystems, gripping/manipulation subsystems, and/or other subsystems of the platform 300, as described below. In this regard, the deck 310 can be stationary as a reference platform, while other components are actuated into position for interacting with elements of the deck 310. Alternatively, the deck 310 can be coupled to one or more actuators (e.g., a conveyer, a sliding drawer, etc.) for positioning elements.

In the embodiment shown in FIGS. 5 and 6, the deck 310 includes a conveying element 312 which functions to bring one or more units of the microwell assembly into alignment with the heating subsystem and/or imaging subsystem described in more detail below. In one variation, the conveying element 312 can include a sliding element (e.g., drawer, tray, etc.) that receives one or more units of the microwell assembly during loading, and transitions, with coupled actuators, the one or more units into alignment with the heating subsystem and/or imaging subsystem during operation for thermocycling and detection. In such variations, the sliding element can include openings that provide access to portions of the microwell assembly units for heating, imaging, sealing, and/or other operations. In another variation, the conveying element 312 can include a belt, robotic arm, rollers, or other conveying element.

In other variations, the deck 310 can additionally or alternatively provide a platform supporting the set of sample processing elements, where the sample processing elements can include disposable and/or reusable components, where the components include containers for containing sample processing materials and/or tools for processing samples (e.g., in relation to fluid handling, in relation to material separation, in relation to heating and cooling, etc.). In embodiments, the deck 310 can support a set of sample processing elements including one or more units of: a reagent cartridge, units of the microwell assembly 100 described above (e.g., in storage, disassembled with separate base substrates 110 and cover layers 210, and in-use positions for sample processing), sample staging containers (for staging samples prior to transfer to the microwell assembly 100), a tool container, and/or other subsystems.

Additionally or alternatively, the deck 310 and/or base 380 can include other suitable components associated with an imaging subsystem 330 (e.g., fluorescence detection subsystems, brightfield camera subsystems, confocal microscope subsystems, spectroscopic detection subsystems, Total Internal Reflection Fluorescence (TIRF) subsystems, Nuclear Magnetic Resonance (NMR) subsystems, Raman Spectroscopy (RS) RS subsystems, cellular phone with optic accessories to improve pixel resolution, etc.), where the imaging subsystem is described in more detail below.

The sample processing elements can be supported in a co-planar manner by the deck 310, or alternatively at different planes. Preferably, discrete elements supported by the deck are non-overlapping, but alternative embodiments of the deck 310 can support the sample processing elements in an overlapping manner (e.g., for conservation of space, etc., for operational efficiency, etc.).

Other aspects of embodiments, variations, and examples of deck-supported elements are described in U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by this reference.

3.2 Actuation Subsystem

As shown in FIG. 6, the platform 300 can include an actuation subsystem 370 (e.g., coupled to a gantry, coupled to the deck 310, coupled to another portion of the platform 300, etc.), which functions to support and/or enable actuation of one or more components to interact with units of the microwell assembly in association with various sample processing and/or interrogation steps.

In variations, the actuation subsystem 370 can provide actuation elements (e.g., jacks, linear actuators, rotary actuators, etc.) configured to move elements of a heating subsystem, imaging subsystem, and/or fluid handling subsystem into communication with units of the microwell assembly during sample processing. Additionally or alternatively, the actuation subsystem 370 can move units of the microwell assembly into communication with elements of the heating subsystem, imaging subsystem, and/or fluid handling subsystem.

Additionally or alternatively, the actuation subsystem 370 can include a gantry, which provides one or more rails/tracks for moving tools, as described in U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by reference, as above.

3.3 Heating Subsystem

As shown in FIGS. 5 and 6, the platform 300 can also include a heating subsystem 365, which functions to transfer heat to and/or from desired regions of the microwell assembly in relation to various workflows described in more detail in Section 4 below. The heating subsystem 365 also functions to apply pressure to the cover layer 210 against the base substrate 110 in order to seal individual microwells and/or sample processing regions, and prevent inter-sample contamination.

As shown in FIGS. 5 and 6, the heating subsystem 365 can include a heating body 366 configured to couple with a portion of the actuation subsystem 370 described above, where the heating body 366 can operate in an extended mode to apply pressure to the cover layer 210 against the base substrate 110, and a retracted mode in which the heating body 366 is retracted away from the microwell assembly. Additionally, the heating body 366 can operate in various heating modes, in order to perform thermocycling of microwell contents and/or other heating and cooling operations. With respect to one such operation mode, the cover layer 210 can include a sealed operation mode in which the cover layer 210 seals individual sample processing regions of the set of sample processing regions, and transfers heat to contents of the set of sample processing regions upon receiving heat from the heating subsystem 365. The heating body 366 can be configured in a manner that provides suitable temperature uniformity at the microwells of the microwell assembly during operation (e.g., with thermal gradients); however, the heating body 366 can alternatively produce other suitable thermal profiles across the microwell assembly. Furthermore, the heating body 366 can include or otherwise be coupled to or in thermal communication with heat dissipation elements (e.g., that dissipate heat by conduction, by convection, etc.) in relation to achieving rapid thermocycling and/or other temperature ramping profiles. The heating subsystem 365 can additionally or alternatively include temperature sensors for achieving precise temperature control for various operations.

Figure 7A:
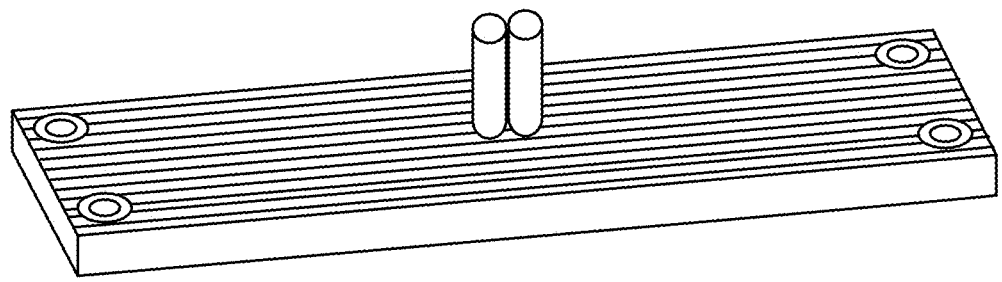
FIGS. 7A-7C depict variations of a heating body, temperature sensor, and other heating subsystem components associated with a platform for automating processing of samples using units of a microwell assembly.
Figure 7B:
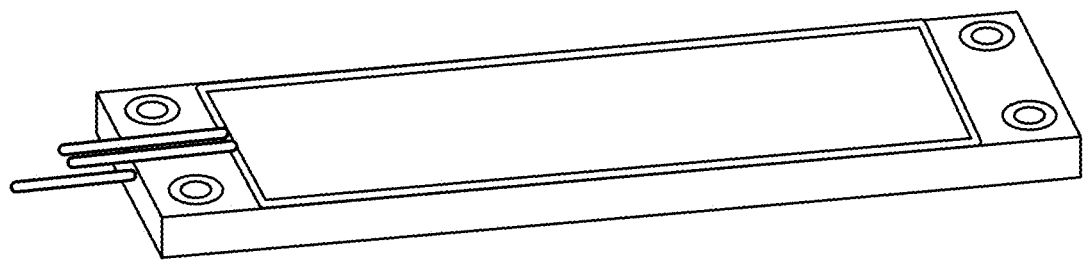
Figure 7C:
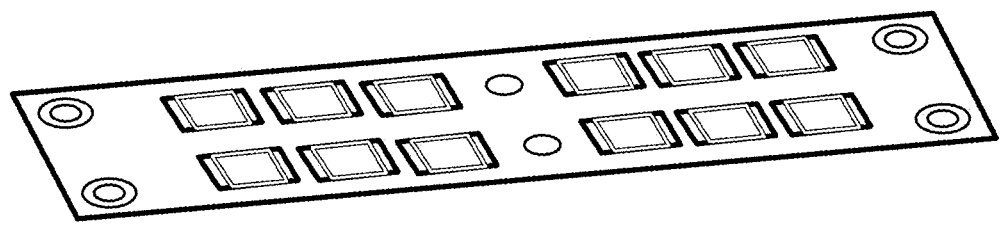

In one variation, as shown in FIG. 7A, the heating body 366 can include an aluminum nitride heater with cooling fins, coupled to a monolithic resistive heater and temperature sensor for achieving precise temperature control for various operations. In another variation shown in FIG. 7B, the heating body 366 can include an aluminum heater coupled to a thin film polymer heater and temperature sensor for achieving precise temperature control for various operations. In another variation shown in FIG. 7C, the heating body 366 can include an aluminum-backed printed circuit board with surface-mounted resistive heaters and temperature sensors with independent control for achieving precise temperature control at one or more regions of the heating body 366 for various operations. However, the heating body 366 can be otherwise configured. Furthermore, as shown in FIG. 5, the heating subsystem 365 can include a fan 367 (or other cooling subsystem components) as a heat dissipation element to allow rapid temperature adjustments to be performed by the system.

The heating subsystem 365 can additionally be designed such that each sample can be individually heated in a controlled manner, to provide individual environments with individually-adjustable temperature incubation profiles. Such a configuration can be accomplished by having individual heater and sensor units arranged in an array corresponding to the array of the sample processing regions. The array of heating units can be coupled to a controller that allows individual electronic addressing, temperature estimation, power actuation, and synchronization to provide individual control in relation to sample heating.

The heating subsystem 365 can additionally or alternatively include embodiments, variations, and examples of elements, as described in U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by reference, as above.

3.4 Imaging Subsystem

As shown in FIGS. 5 and 6, the platform 300 can include an imaging subsystem 375 comprising an imager 376 coupled to an imager stage 377, where the imaging subsystem 375 functions to enable performance of rapid detection of signals generated from contents of microwells of the sample processing regions of the microwell assembly. The imaging subsystem 375 functions to provide capability for real-time and/or end-point fluorescence, in order to enable performance of staged and/or multiple assays per sample. In variations, however, the imaging subsystem 375 can be substituted with or supplemented by optical detection elements configured to detect optical signals from contents of the microwell assembly without generation of images.

In variations, the imaging subsystem 375 includes optics components (e.g., filters, mirrors, lenses, etc.) and optical sensors configured for detection of multiple colors/wavelength ranges of light from samples at the microwell assembly. In a specific example, the imaging subsystem 375 is configured for 6-color fluorescence with melt analysis for up to three melts per color, thereby enabling up to 18 assays per sample; however in other variations, the imaging subsystem 375 can be configured for another suitable number of colors/wavelength ranges (e.g., between 3 and 15 wavelength ranges) and/or number of melt analyses (e.g., between 2 and 6 melt analyses) per color. Furthermore, emission and/or excitation filters can be included, where the filters provide the ability to further multiplex sample processing and target detection.

In variations, the imaging subsystem 375 can additionally or alternatively include illumination elements (e.g., LEDs, other illuminators) for transmitting excitation wavelengths of light toward samples at units of the microwell assembly, for bright-field imaging, and/or for other suitable purposes.

As shown in FIGS. 5 and 6, the imager 376 can be coupled to an imager stage 377 for actuation of the imager 376 relative to one or more units of the microwell assembly positioned at the deck (e.g., by way of the drawer described above), and/or for focusing operations. However, the imager 376 and imager stage 377 can alternatively be configured in another suitable manner. Furthermore, the imager 376 can be configured to oppose the heating subsystem across units of the base substrate 110/cover layer 210 assembly. Additionally, the imager 376 can be positioned under the conveyer 312 in some variations. However, the imager 376 can be otherwise positioned in alternative variations.

The imaging subsystem 375 can additionally or alternatively include embodiments, variations, and examples of elements, as described in U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/115,059 filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017; which are each incorporated in their entirety by reference, as above.

3.1.4 Other Platform Elements

In variations, the platform 300 (e.g., at base 380) can support control and processing architecture for one or more system functions including: fluid delivery for sample processing; fluid level sensing; actuation of various subsystems; thermocycling and/or other heating or cooling functions; magnetic actuation subsystems for enhancement of mixing in microwells; magnetic actuation subsystems for targeted delivery of magnetic beads for specific reagent bead delivery, functions for control of the actuation subsystem 370; functions involving receiving sensor signals and returning outputs; functions involving receiving sensor signals and executing various actions; functions associated with system power management; functions associated with system status indication elements (e.g., lights, audio output devices, visual output devices, etc.); functions associated with system input devices (e.g., buttons, keyboards, keypads, mice, joysticks, switches, touch screens, etc.); functions associated with display devices; functions associated with system data storage devices; functions associated with system transmission devices (e.g., wired transmission devices, wireless transmission devices, etc.); and other suitable functions. In variations, the platform 300 can thus support an electronics subsystem (e.g. printed circuit board (PCB) elements, power source, communication module, encoder, etc.) associated with a processing architecture (e.g. onboard the system, separate from the system, etc.), or any other suitable component, where the processing architecture can include any or all of: processors (e.g. microprocessors), controllers (e.g. microcontrollers), memory, storage, software, firmware, or any other suitable component. Additionally, the processing subsystem can include machine vision architecture, which functions to read tags, verify protocols, perform error detection (e.g. detect that reagents do not match an assigned protocol), or perform any other function.

Embodiments, variations, and examples of additional elements are further described in U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; U.S. application Ser. No. 15/815,532, filed 16 Nov. 2017; U.S. application Ser. No. 16/115,370, filed 28 Aug. 2018, U.S. application Ser. No. 16/564,375, filed 9 Sep. 2019, and U.S. application Ser. No. 16/816,817, filed 12 Mar. 2020, as incorporated by reference above. However, the platform can additionally or alternatively include other suitable elements.

4. METHODS AND APPLICATIONS OF USE

Figure 8:
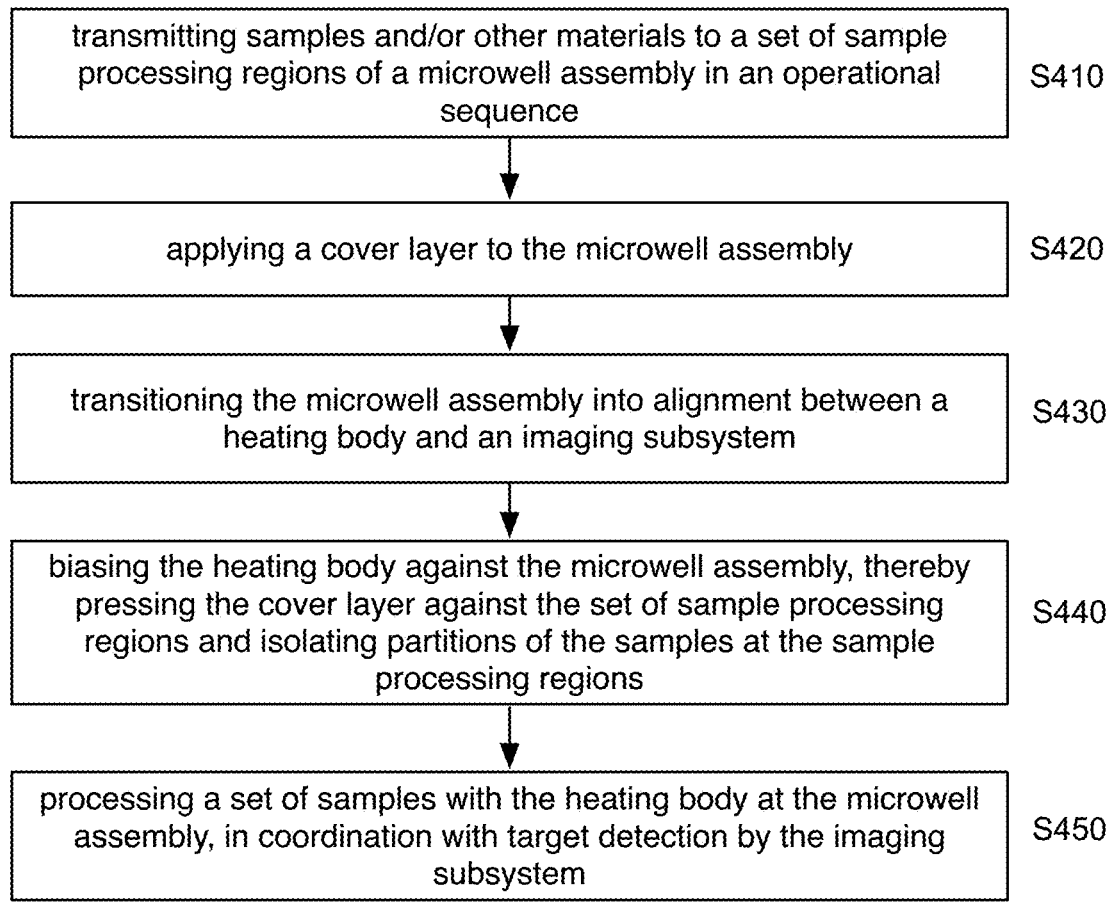
FIG. 8 depicts a flow chart of an embodiment of a method for sample processing and target detection.

As shown in FIG. 8, an embodiment of a method 400 for target detection and characterization can include: transmitting samples (e.g., a set of different samples, a set of aliquots of the same sample, etc.) and/or other materials to a set of sample processing regions of a microwell assembly in an operational sequence S410; applying a cover layer to the microwell assembly S420; transitioning the microwell assembly into alignment between a heating body and an imaging subsystem S430; biasing the heating body against the microwell assembly, thereby pressing the cover layer against the set of sample processing regions and isolating partitions of the samples at the sample processing regions S440; and processing a set of samples with the heating body at the microwell assembly, in coordination with target detection by the imaging subsystem S450.

Additionally or alternatively, the method 400 can include any or all of the processes described in U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; U.S. application Ser. No. 15/815,532, filed 16 Nov. 2017; U.S. application Ser. No. 16/115,370, filed 28 Aug. 2018, U.S. application Ser. No. 16/564,375, filed 9 Sep. 2019, and U.S. application Ser. No. 16/816,817, filed 12 Mar. 2020, which are each incorporated in their entirety by this reference.

In embodiments, the method 400 can enable processing of small volume sample partitions efficiently, with high dynamic range (e.g., 5 to 10 logs of dynamic range, more than 10 logs of dynamic range, etc.), using a relatively few number of partitions (e.g., under 1000 partitions of a microwell assembly having a small footprint). In particular, such a configuration produces efficiencies in thermocycling (e.g., reduced ramp times) as well as reductions in scanning times by an imaging subsystem, in order to achieve results rapidly. In embodiments, such a microwell assembly can enable rapid thermocycling with heating only from one side of the microwell assembly, thereby achieving end-point PCR results within 20 minutes (or less) in examples, with slightly longer durations of time to results if scanning between thermocycling cycles is implemented. However, heating from both sides can also be implemented.

Additionally, with use of microwell subarrays having a gradient in microwell characteristic dimensions, the method 400 can enable rapid generation of preliminary results, with reading of signals (e.g., fluorescence-based signals) from individual subarrays associated with a sample. For instance, by reading signals from the largest subarrays carrying the largest sub-volume of a particular sample in real-time, representative averaged results for target detection and characterization can be generated with high accuracy prior to completion of the assay(s). As such, the method 400 can include operation modes in which, upon distribution of a sample across the set of microwell subarrays and processing of the sample within the set of microwell subarrays in parallel, preliminary representative results are produced from averaged signals of a microwell subarray (e.g., the microwell subarray with wells of the largest characteristic volume) of the set of microwell subarrays, in order to provide preliminary results with suitable confidence limits.

Additionally, sealing of the microwell assembly using the heating body and the cover layer functions to mitigate bubble formation effects, thereby solving such issues.

Additionally, embodiments of the method 400 can provide real-time integration during fluorescence generation per individual microwell and per sample.

For instance, acquiring and integrating real-time fluorescence signal information generated from contents of individual microwells and/or per sample during amplification reactions can provide information (e.g., in a report) to distinguish between specific and non-specific amplification. Furthermore, parameters associated with quantitative PCR (qPCR) can be determined from real-time signal integration across microwell array subsets, in a manner that significantly reduces time durations prior to result provision.

In particular, with regard to parameters associated with threshold cycle/quantification cycle (e.g., $C_t$, $C_p$, Take-off point (TOP), $C_q$) at which a reaction reaches fluorescent intensity above background levels or another suitable threshold, values calculated from real-time signal integration is evident at thermal cycles prior to that programmed for end-point reading, such that the time to result can be significantly reduced. Additionally or alternatively, acquiring and integrating real-time fluorescence changes (e.g., decreasing fluorescence) detected from individual microwells and/or samples during denaturation and melting reactions can provide information regarding the target and sequence that was amplified. This assay identification based on melt-curve analysis further expands the assay multiplexing capabilities. As such, real-time integration of fluorescent signals and/or non-fluorescent signals from the set of sample processing regions can be used to detect when signals (e.g., fluorescent signals) cross relevant thresholds (e.g., with respect to changes in fluorescence).

Furthermore, analyses can be generated based on information acquired throughout the volume of each partition and/or based on information acquired from a particular surface of a partition. In one such application, detection of binding of a specific product to a surface can be performed independently of a volumetric analysis (e.g., in relation to structures described above for capture of target and/or non-target material at microwell surfaces).

Embodiments, variations, and examples of the method 400 are preferably performed with an embodiment, variation, or example of the systems described above (e.g., in relation to transmission of content between various elements and/or sample processing) but can additionally or alternatively be performed with any other suitable system. The method 400 is further preferably at least partially automated (e.g., requires user to load reagents and select a protocol, requires no user intervention, etc.), but one or more portions can additionally or alternatively be manually performed (e.g., for quality control steps, for all protocols, for rare protocols, etc.).

In variations, the method 400 can be adapted for detection of target material from samples in a rapid and multiplexed manner, where samples include tissues, tissue components, single cells, organelles, viruses, virus components, proteins, peptides, other products released from single cells/tissues, bacteria, other organisms, nucleic acid material (e.g., cellular DNA, cell-free DNA, RNAs, etc.) and/or other material. Targets can include analytes, chemicals, nucleic acid material, proteins, amino acids, peptides, and/or other suitable target material.

Specific workflows associated with the method 400 and system elements described above are described in further detail below, where samples can be processed according to the workflows.

4.1 Method Example Workflow for Small Volume PCR of Multiple Samples in Parallel As shown in FIG. 9, Block S410 recites: transmitting samples and/or other materials to a set of sample processing regions of a microwell assembly in an operational sequence. In embodiments, the system can position a set of sample processing elements, including units of a microwell assembly at a deck of a sample processing system, in preparation for processing samples in subsequent steps of the method 400. The system can configure, using the actuation subsystem described above and/or by manual actions by a system operator, the set of sample processing elements for downstream processing steps. In other variations, Step S410 can configure sample processing elements in another suitable manner, for processing multiple samples in parallel. In preparing for downstream sample processing operations, Step S410 can include transitioning a base substrate of a unit of a microwell assembly to a liquid loading position of the platform, and reading, using a camera of the platform, a plate identifier. The system can then match the plate identifier with identifiers of samples for processing, in order to verify that the correct samples are being processed, and to affiliate any sample processing results with the run associated with the plate identifier. Step S410 can, however, include other run preparation steps in other variations.

Step S410 can additionally or alternatively include other sample preparation steps. For instance, Step S410 can include operations for processing sample material derived from tissue, blood, raw materials, or other biological materials (example sample types of which are described above) such that they can be distributed into the set of sample processing regions of the base substrate of the microwell assembly. In variations, step S410 can include one or more of: mixing a volume (of each sample being processed with media, reagents (e.g., for probe attachment, for barcode attachment, etc.), buffer, other processing materials in dry or liquid form or other materials; filtering samples (e.g., to remove particulates that may affect loading of samples at microwells, distribution of samples uniformly across microwells having different characteristic dimensions, clogging, detection, etc.), where limiting particulate sizes can be covered based upon pitch between adjacent microwells, washing samples; transferring the set of samples to a set of sample processing regions of a base substrate of the microwell assembly; and any other suitable sample preparation step. Step S410 can be performed using fluid handling elements of the platform described in Section 3 above, or using other suitable apparatus components.

In relation to transferring samples in Step S410, transfer can be implemented using a pre-determined delivery of the samples in droplet-form across respective microwell surfaces associated with each sample, by way of capillary flow from one end of a sample processing region as enabled by spacing between the base substrate and cover layer of the microwell assembly applied in Step S420. In variations, each of the set of samples being processed can be transferred to be received at the sample processing regions of the base substrate in sequence. Alternatively, the set of samples can be dispensed into the sample processing regions of the base substrate simultaneously (e.g., using a multi-head fluid dispensing apparatus, using other apparatus). As such, Step S410 can include automatically distributing the set of samples across the gradients of the set of sample processing regions in parallel according to one or more methods.

Step S420 recites: applying a cover layer to the microwell assembly, which functions to protect and facilitate maintenance of a proper environment for the set of samples during downstream processing and thermocycling steps. In variations, Step S420 can be performed using the elements (e.g., actuation of a heating block, actuation of modified gripping elements, etc.) coupled to the actuation subsystem of the platform described in Section 3 above and shown in FIGS. 6 and 7, or using other suitable apparatus. Step S420 can, however, be implemented in another suitable manner.

Step S430 recites: transitioning the microwell assembly into alignment between a heating body and an imaging subsystem, which functions to stage the microwell assembly for rapid thermocycling and target detection from each partition (e.g., with real-time signal integration of fluorescent signals, colorimetric signals, other signals) in association with various assays (e.g., digital PCR assays, qPCR assays, MPN assays, etc.). Step S430 can be implemented using the conveying element (e.g., sliding drawer) of the deck described in Section 3 above, a robotic arm, other actuation subsystems, or another suitable element.

Step S440 recites: biasing the heating body against the microwell assembly, thereby pressing the cover layer against the set of sample processing regions and isolating partitions of the samples at the sample processing regions. Step S440 functions to seal each sample processing region and/or partition, to prevent cross-contamination and/or mitigate effects of bubble formation. In Step S440, the system can apply heat through the heating block to the cover layer, thereby promoting sealing of partitions of the microwell assembly by the cover layer using a thermal bond. Additionally or alternatively, the cover layer can include an adhesive portion, such that pressing the cover layer against the base substrate of the microwell assembly seals the partitions of the microwell assembly. Additionally or alternatively, another suitable portion of the sample processing platform described in Section 3 above can press the cover layer against the set of sample processing regions of the base substrate prior to downstream processing steps.

Step S450 recites: processing a set of samples with the heating body at the microwell assembly, in coordination with target detection by the imaging subsystem S450. Block S450 functions to efficiently thermocycle samples using the unique configuration of the microwell assembly, and provide reduced scanning times by the imaging subsystem, in order to achieve results rapidly. In embodiments, step S450 applies heating only from one side of the microwell assembly in coordination with scanning of the microwell assembly partitions, thereby achieving end-point PCR results within 20 minutes (or less) in examples, with slightly longer durations of time to results if scanning between thermocycling cycles is implemented. However, heating from both sides can also be implemented in step S450.

In variations, step S450 can implement illumination components and optics components of the imaging subsystem, in coordination with image analysis architecture of the computing components described in Section 3 above to provide capability for real-time or end-point fluorescence, in order to enable performance of multiple assays per sample. In more detail, step S450 can provide detection of multiple colors/wavelength ranges of light from samples undergoing reactions/processing at each microwell assembly of each sample processing region. As such, the method can support operation modes in which multi-color fluorescence signals for a set of colors, with a set of melts/melting temperatures corresponding to each of the set of colors, the set of melting temperatures corresponding to different targets of a sample, can be returned to provide multiplexed target detection in a rapid and efficient manner.

In variations, the set of colors can include up to 6 color/wavelength ranges for detection; however, in alternative variations, the set of colors can include greater than 6 color/wavelength ranges for detection. In variations, each of the set of colors can provide analyses for up to 3 melting/denaturation points associated with particular targets; however, each of the set of colors can provide analyses for greater than 3 melting/denaturation points associated with target material of samples being processed. In variations, color channels implemented can be associated with excitation and/or emission wavelengths in the visible spectrum and/or outside the visible spectrum of electromagnetic radiation.

With respect to target material tagging, fluorophore families implemented can be associated with chemical families including: xanthene derivatives, cyanine derivatives, squaraine derivates, squaraine rotaxane derivatives, naphthalene derivatives, coumarin derivatives, oxadiazole derivatives, anthracene derivatives, pyrene derivatives, oxazine derivatives, acridine derivatives, arylmethine derivatives, tetrapyrrole derivatives, dipyrromethene derivatives, and/or other chemicals. Such fluorophores can further be attached to other functional groups as needed for tagging of target material.

In examples, nucleic acid dyes for tagging of target material and detection can include one or more of: Hoechst dyes, DAPI dyes, SYTOX dyes, chromomycin dyes, mithramycin dyes, YOYO dyes, ethidium bromide dyes, acridine orange dyes, TOTO dytes, thiazole dyzes, CyTRAK dyes, propidium iodide dyes, LDS dyes, and/or other dyes.

In examples, cell function dyes for tagging of target material and detection can include one or more of: indo-1, Fluo-3, Fluo-4, DCFH, DHR, SNARF, and/or other dyes.

In examples, fluorescent proteins for tagging of target material and detection can include one or more of: CFP, EBFP, Azurite, T-Sapphire, cerulean, mCFP, mTurquoise, ECFP, CyPet, and/or other fluorescent proteins.

In variations, in relation to Step S450, the imaging subsystem can provide operation modes for scanning/providing optical detection of fluorescence, colorimetric changes, and/or other signals simultaneously for all sample processing regions of the microwell assembly, and/or sequentially for one or more sample processing regions of the microwell assembly. Additionally or alternatively, the imaging subsystem can provide operation modes for scanning/providing optical detection of fluorescence, colorimetric changes, and/or other signals simultaneously for all microwell subarrays of a sample processing region, and/or sequentially for one or more microwell subarrays of a sample processing region.

In variations involving coordination between imaging or other optical detection and heating associated with a reaction, Step S450 can include performing imaging or optical detection between (e.g., prior to, after) individual thermocycling runs or other heating/cooling phases. Additionally or alternatively, Step S450 can include performing imaging or optical detection contemporaneously with (e.g., simultaneously with, with overlap in relation to) individual thermocycling runs or other heating/cooling phases. Imaging or optical detection can be performed for multiple colors/wavelength ranges simultaneously, or alternatively for individual colors/wavelength ranges in sequence. As such, in step S450, the system can controllably thermocycle samples using a suitable heating and/or cooling profile, using the heating body, associated temperature sensors, heat dissipation elements, and associated control circuitry, in coordination with imaging.

In variations of Step S450, the imaging subsystem, in coordination with coupled signal processing architecture, can perform real-time signal integration of signals, in relation to various thresholds. For instance, in relation to a threshold at which a reaction produces signals with intensity above background levels, the imaging subsystem, in coordination with coupled signal processing architecture can perform an action (e.g., return a notification, return an analysis) when signals from microwells (e.g., a microwell subarray with the largest microwells, a microwell subarray with microwells of other dimensions, etc.) cross the threshold, are greater than the threshold by a desired magnitude or factor, or are less than the threshold (e.g., in relation to melting and denaturing). The action can be performed when signals from individual microwells and/or average signals from subsets of microwells change relative to the threshold.

As such, in one variation, the imaging subsystem can detect signals from individual microwell subarrays for each sample processing region, average the signals with respect to groupings of microwells, and compare individual or averaged signals to respective thresholds. Once results from individual and/or grouped microwells of the sample processing region(s) pass suitable threshold conditions, the system can return preliminary results with suitable confidence prior to end-point, such that the preliminary results can be provided in an efficient manner.

In a specific example, the imaging subsystem can be configured for 6-color fluorescence with melt analysis for up to three melts per color, thereby enabling up to 18 assays per sample; however in other variations, the imaging subsystem can be configured for another suitable number of colors/wavelength ranges and/or number of melt analyses per color, thereby enabling a large number of assays to be performed per sample in a multiplexed manner. In addition, the number of assays performed per color in each sample could be increased by using different levels of probe amplitudes. By using barcoded beads containing target specific primers or probes, we can further increase the number of assays performed per sample, embodiments, variations, and examples of which are described in U.S. application Ser. No. 16/890,417 filed on 2 Jun. 2020, which is herein incorporated in its entirety by this reference.

In examples, in a coordinated manner, the system can also perform scanning operations using the imaging subsystem. Scanning can be performed after thermocycling is complete, and/or in coordination with cycles of thermocycling (e.g., in between cycles) to generate data in a dynamic manner as reactions progress. In one such application, with use of microwell subarrays having a gradient in microwell characteristic dimensions, step S450 can enable rapid generation of preliminary results, with reading of signals (e.g., fluorescence-based signals) from individual subarrays associated with a sample. For instance, by reading signals from the largest subarrays carrying the largest sub-volume of a particular sample in real-time, representative averaged results for target detection and characterization can be generated with high accuracy prior to completion of the assay(s) in step S450.

In examples, Step S450 can achieve result readout within 20 minutes of sample handling by the system for end-point PCR, or within 30 minutes if scanning by the imaging subsystem between thermocycling cycles is implemented.

In variations of step S450, the system can process images of the microwell assembly, with one or more transformation algorithms (e.g., filtering operations, fitting operations, microwell-recognition operations, registration operations, background-reduction operations, signal amplifying operations, etc.) for detection of fluorescent/colorimetric signals and associated characteristics (e.g., intensity), and/or perform other suitable image processing operations. The system can then generate analyses based upon various methods described in applications incorporated by reference above.

The system embodiment(s) can, however, be configured to implement other workflows including variations of those described, and/or other workflows. For instance, applicable workflows can include one or more of: PCR-assays not discussed above, Loop-mediated isothermal amplification (LAMP) assays, recombinase polymerase reactions, and/or other amplification reactions. Additionally or alternatively, workflows can be associated with other melt curve analyses not discussed above, for analyzing purity of reaction products.

5. CONCLUSION

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

What is claimed is:

1. A system for target detection, the system comprising:
a base substrate shaped as a microwell plate;
an array of sample processing regions comprising at least three sample processing regions defined at a top surface of the base substrate, wherein a sample processing region of the array of sample processing regions comprises:
  a set of microwell subarrays arranged to provide up to a 9 log dynamic range for a polymerase chain reaction (PCR) process, based upon distribution of the set of microwell subarrays in a gradient by volumetric capacity between a first end and a second end of the sample processing region, the set of microwell subarrays comprising:
    an initial subarray with microwells individually having a first volumetric capacity and first cross section smaller than microwells of all other subarrays of the set of microwell subarrays, and
    a terminal subarray with microwells individually having a second volumetric capacity and second cross section greater than microwells of all other subarrays of the set of microwell subarrays, wherein the first volumetric capacity and the second volumetric capacity each fall within a range from 0.1 nL to 100 nL, and
  a boundary recessed into the base substrate, surrounding the sample processing region as a moat, and separating the sample processing region from adjacent sample processing regions of the array of sample processing regions;
a heating subsystem comprising a heating body and a temperature sensor;
a cooling subsystem; and
a controller coupled to the heating subsystem and the cooling subsystem for performance of the PCR process.

2. The system of claim 1, wherein the base substrate is configured to absorb inhibitors of target detection reactions within the array of sample processing regions, wherein said inhibitors comprise RNases, DNases, and proteinases.

3. The system of claim 1, wherein the array of sample processing regions comprises from 3 to 96 sample processing regions.

4. The system of claim 1, wherein each of the set of microwell subarrays comprises from 10 through 500,000 microwells.

5. The system of claim 1, wherein the initial microwell subarray occupies a first footprint of the base substrate, and wherein the terminal microwell subarray occupies a second footprint of the base substrate larger than the first footprint.

6. The system of claim 1, wherein the boundary comprises a recessed channel operable to receive sample overflow.

7. The system of claim 1, further comprising a cover layer biased against the base substrate, the cover layer sealing individual sample processing regions of the array of sample processing regions.

8. The system of claim 7, wherein a surface of the cover layer facing the array of sample processing regions of the base substrate has a surface roughness less than 5 microns and is configured to reflect light toward interior volumes of the array of sample processing regions.

9. The system of claim 7, wherein the cover layer comprises a photo-thermal coating configured to receive incident light of a specified wavelength range, transform incident light into heat, and transmit said heat to contents of the array of sample processing regions.

10. The system of claim 7, wherein the cover layer comprises a first locking portion complementary to a second locking portion of the base substrate, wherein the cover layer is composed of an elastomeric material, and wherein mating of the cover layer to the base substrate spreads a sample across the sample processing region.

11. The system of claim 7, wherein the cover layer seals individual sample processing regions of the array of sample processing regions, and transfers heat to contents of the array of sample processing regions upon receiving heat from a heating subsystem.

12. The system of claim 7, wherein the cover layer is separated from the base substrate by a film layer.

\* \* \* \* \*